US009278083B2

(12) United States Patent
Gutman et al.

(10) Patent No.: US 9,278,083 B2
(45) Date of Patent: Mar. 8, 2016

(54) METHODS FOR PURIFYING TRANS-(−)-Δ⁹-TETRAHYDROCANNABINOL AND TRANS-(+)-Δ⁹-TETRAHYDROCANNABINOL

(71) Applicant: SVC Pharma LP, Spring Valley, NY (US)

(72) Inventors: Arie L. Gutman, Haifa (IL); Marina Etinger, Nesher (IL); Irina Fedotev, Haifa (IL); Ram Khanolkar, Coventry, RI (US); Gennady A. Nisnevich, Haifa (IL); Boris Pertsikov, Nesher (IL); Igor Rukhman, Yokneam (IL); Boris Tishin, Haifa (IL)

(73) Assignee: SVC Pharma LP, Spring Valley, NY (US)

( * ) Notice: Subject to any disclaimer, the term of this patent is extended or adjusted under 35 U.S.C. 154(b) by 0 days.

(21) Appl. No.: 14/596,034

(22) Filed: Jan. 13, 2015

(65) Prior Publication Data
US 2015/0126596 A1    May 7, 2015

Related U.S. Application Data

(60) Division of application No. 13/774,955, filed on Feb. 22, 2013, now Pat. No. 8,937,097, which is a continuation of application No. 11/791,415, filed as application No. PCT/EP2005/012378 on Nov. 18, 2005, now Pat. No. 8,383,842.

(60) Provisional application No. 60/630,556, filed on Nov. 22, 2004.

(51) Int. Cl.
*A61K 31/352* (2006.01)
*C07D 311/78* (2006.01)
*C07D 311/80* (2006.01)

(52) U.S. Cl.
CPC ............ *A61K 31/352* (2013.01); *C07D 311/80* (2013.01)

(58) Field of Classification Search
CPC ........................... A61K 31/352; C07D 311/78
USPC ........................ 549/356, 385; 514/451, 454
See application file for complete search history.

(56) References Cited

U.S. PATENT DOCUMENTS

| | | |
|---|---|---|
| 3,507,885 A | 4/1970 | Fahrenholtz et al. |
| 3,560,528 A | 2/1971 | Petrzilka |
| 3,668,224 A | 6/1972 | Petrzilka |
| 3,854,480 A | 12/1974 | Zaffaroni |
| 4,025,516 A | 5/1977 | Razdan et al. |
| 4,381,399 A | 4/1983 | Olsen et al. |
| 4,861,598 A | 8/1989 | Oshlack |
| 4,970,075 A | 11/1990 | Oshlack |
| 5,227,537 A | 7/1993 | Stoss et al. |
| 5,389,375 A | 2/1995 | ElSohly |
| 5,508,037 A | 4/1996 | ElSohly |
| 5,958,452 A | 9/1999 | Oshlack et al. |
| 5,965,161 A | 10/1999 | Oshlack et al. |
| 6,136,839 A | 10/2000 | Isakson et al. |
| 6,328,992 B1 | 12/2001 | Brooke et al. |
| 6,365,416 B1 | 4/2002 | Elsohly et al. |
| 6,383,513 B1 | 5/2002 | Watts et al. |
| 6,403,126 B1 | 6/2002 | Webster et al. |
| 6,509,005 B1 | 1/2003 | Peart et al. |
| 6,555,139 B2 | 4/2003 | Sharma |
| 6,620,351 B2 | 9/2003 | Gupta et al. |
| 6,642,275 B2 | 11/2003 | Alfonso et al. |
| 6,703,418 B2 | 3/2004 | Plasse |
| 6,706,281 B2 | 3/2004 | Oshlack et al. |
| 6,713,048 B2 | 3/2004 | Peart et al. |
| 6,730,330 B2 | 5/2004 | Whittle et al. |
| 6,733,783 B2 | 5/2004 | Oshlack et al. |
| 6,747,058 B1 | 6/2004 | Dedhiya et al. |
| 6,814,072 B1 | 11/2004 | Seppälä |

(Continued)

FOREIGN PATENT DOCUMENTS

| | | |
|---|---|---|
| CA | 2469490 A1 | 7/2003 |
| CA | 2499492 A1 | 1/2004 |

(Continued)

OTHER PUBLICATIONS

U.S. Appl. No. 60/691,361, filed Jun. 16, 2005, Kupper.
U.S. Appl. No. 60/726,509, filed Oct. 12, 2005, Kupper.
Archer et al.,"Carbon-13 nuclear magnetic resonance spectroscopy of naturally occurring substances. 47. Cannabinoid compounds," *J Org. Chem.* 42(3):490-495 (1977).
Augurell et al., "Pharmacokinetics and Metabolism of Δ¹-Tetrahydrocannabinol and Other Cannabinoids with Emphasis on Man," *Pharmacol. Revs.* 38(1):21-43 (1986).
Avis et al., "Parenteral Preparations," in *Remington: The Science and Practice of Pharmacy*, 20$^{th}$ ed. Ch. 41, pp. 780-806, A.R. Gennaro (ed.), Lippincott (2000).
Bhatta (Commentary by Kaladhara Bhatta), "Formulation ID: RS4/ 250; Formulation Name: Bhanga Saka," Chaukhambha Krishnadas Academy, Varanasi, 3$^{rd}$ Ed., p. 72 (2003 (Exhibit 3 of the Third Party Observation (Ref. C20)).

(Continued)

Primary Examiner — Golam M M Shameem
(74) Attorney, Agent, or Firm — Dechert LLP

(57) ABSTRACT

Methods for making trans-(−)-Δ⁹-tetrahydrocannabinol and trans-(+)-Δ⁹-tetrahydrocannabinol are disclosed herein. In one embodiment, a trans-(−)-Δ⁹-tetrahydrocannabinol composition is prepared by allowing a composition comprising (±)-Δ⁹-tetrahydrocannabinol to separate on a chiral stationary phase to provide a trans-(−)-Δ⁹-tetrahydrocannabinol composition comprising at least about 99% by weight of trans-(−)-Δ⁹-tetrahydrocannabinol based on the total amount of trans-(−)-Δ⁹-tetrahydrocannabinol and trans-(+)-Δ⁹-tetrahydrocannabinol. The invention also relates to methods for treating or preventing a condition such as pain comprising administering to a patient in need thereof an effective amount of a trans-(−)-Δ⁹-tetrahydrocannabinol having a purity of at least about 98% based on the total weight of cannabinoids.

18 Claims, No Drawings

(56) References Cited

U.S. PATENT DOCUMENTS

| | | | |
|---|---|---|---|
| 7,186,850 B2 | 3/2007 | Silverberg | |
| 7,449,589 B2 | 11/2008 | Geisler et al. | |
| 7,524,881 B2 | 4/2009 | Goodwin et al. | |
| 8,383,842 B2* | 2/2013 | Gutman | A61K 31/352 549/390 |
| 8,937,097 B2* | 1/2015 | Gutman | A61K 31/352 514/451 |
| 2003/0050334 A1 | 3/2003 | Murty et al. | |
| 2003/0229027 A1 | 12/2003 | Eissens et al. | |
| 2004/0034108 A1 | 2/2004 | Whittle | |
| 2004/0069798 A1 | 4/2004 | Grey et al. | |
| 2004/0138293 A1 | 7/2004 | Werner et al. | |
| 2004/0143126 A1 | 7/2004 | Webster et al. | |
| 2004/0209944 A1 | 10/2004 | Plasse | |
| 2004/0229939 A1 | 11/2004 | Chowdhury et al. | |
| 2006/0167084 A1 | 7/2006 | Dudley | |
| 2007/0072939 A1 | 3/2007 | Kupper | |
| 2008/0008754 A1 | 1/2008 | Lewis et al. | |
| 2008/0275237 A1 | 11/2008 | Arslantas et al. | |

FOREIGN PATENT DOCUMENTS

| | | |
|---|---|---|
| CA | 2770448 A1 | 5/2004 |
| EP | 2289509 A2 | 2/2011 |
| EP | 1824475 B1 | 3/2011 |
| EP | 2356987 A1 | 8/2011 |
| WO | WO 03/013538 A1 | 2/2003 |
| WO | WO 2005/044093 A2 | 5/2005 |
| WO | WO 2009/018389 A1 | 2/2006 |
| WO | WO 2006/053766 A1 | 5/2006 |
| WO | WO 2006/133941 A3 | 3/2007 |

OTHER PUBLICATIONS

Block, "Medicated Topicals," in *Remington: The Science and Practice of Pharmacy*, 20th ed. Ch. 44, pp. 836-857, A.R. Gennaro (ed.), Lippincott (2000).
Buchwald et al., "Long-term, Continuous Intravenous Heparin Administration by an Implantable Infusion Pump in Ambulatory Patients with Recurrent Venous Thrombosis," *Surgery* 88:507-516 (1980).
Caverro et al., "Effects of (−)-$\Delta^9$-(trans)-Tetrahydrocannabinol on Regional Blood Flow in Anesthetized Dogs," *Eur. J. Pharmacol.* 20:373-376 (1972).
Chang et al., "A Prospective Evaluation of $\Delta$-9-Tetrahydrocannabinol as an Antiemetic in Patients Receiving Adriamycin and Cytoxan Chemotherapy," *Amer. Cancer Soc.* 47:1746-1751 (1981).
Communication dated Apr. 28, 2008 from EPO re application No. 06754384.
Communication dated Apr. 2, 2009 from EPO re application No. 06754384.
Communication dated Apr. 26, 2010 from EPO re application No. 06754384.
Communication dated Jul. 12, 2011 from EPO re application No. 10179360.
Communication dated Jul. 19, 2011 from EPO re application No. 10179374.
Communication dated Aug. 19, 2013 from EPO re application No. 10179374.
Communication dated Sep. 4, 2007 from EPO re application No. 05807597.
Communication dated Mar. 25, 2008 from EPO re application No. 05807597.
Communication dated Sep. 5, 2008 from EPO re application No. 05807597.
Communication dated Jun. 10, 2009 from EPO re application No. 05807597.
Communication Pursuant to Article 94(3) EPC [EPO Official Action in Response to Third Party Observation] for European Patent Application No. 10011148.3 dated Jan. 3, 2012.
Communication Pursuant to Rule 114(2) EPC [Notice of Third Party Observation] for European Patent Application No. 10011148.3 dated Nov. 4, 2011, including Annexes I, II, and III.

During et al., "Controlled Release of Dopamine from a Polymeric Brain Implant: In Vivo Characterization," *Ann. Neurol.* 25:351-356 (1989).
Dwivedi, "Residual Solvent Analysis in Pharmaceuticals," *Pharmaceut. Technol.* pp. 42, 44 & 46 (Nov. 2002).
Ekert et al., "Amelioration of cancer chemotherapy-induced nausea and vomiting by delta-9-tetrahydrocannabinol," *Med. J. Aust.* 2:657-659 (1979).
Entry at http://www.nlm.nih.gov/cgi/mesh/2009/MB_cgi?mode=&term=Tetrahydrocannabinol dated 2009 "MeSH".
Fahrenholtz et al., "Total synthesis of (+−)-$\Delta$-9-tetrahydrocannabinol and four of its isomers;" *JACS* 89(23):5934-5941 (1967).
Fairbairn et al., "The stability of cannabis and its preparations on storage," *J Pharm. Pharmacol.* 28:1-7 (1976).
Francotte, "Enantioselective chromatography as a powerful alternative for the preparation of drug enantiomers," *J Chromatography A* 906:379-397 (2001).
Gaoni et al., "Isolation, Structure, and Partial Synthesis of an Active Constituent of Hashish," *J. Amer. Chem. Soc.* 86:1646-1647 (1964).
Gaoni et al., "Hashish-VII the isomerization of cannabidiol to tetrahydrocannabinols," *Tetrahedron* 22:1481-1488 (1966).
Gaoni et al., "Isolation and structure of $\Delta^1$-tetrahydrocannabinol and other neutral cannabinoids from hashish," *JACS* 93(1):217-224 (1971).
Goodson, "Dental Applications," pp. 115-138 in *Medical Applications of Controlled Release*, vol. 2 , *Applications and Evaluation*, Langer and Wise, Eds., CRC Press (1984).
Howard et al., "Intracerebral drug delivery in rats with lesion-induced memory deficits," *J. Neurosurg.* 71:105-112 (1989).
International Preliminary Report on Patentability for PCT/EP2005/012378 completed Nov. 16, 2006.
International Preliminary Report on Patentability for PCT/EP2006/005761 issued Dec. 17, 2007.
Isbell, "Effects of (−)$\Delta^9$-Tetrahydrocannabinol in Man," *Psyohopharmacologia (Berl.)* 11:184-188 (1967).
Jones et al., "Relative Pharmacological Potency in Mice of Optical Isomers of $\Delta^1$-Tetrahydrocannabinol," *Biochem. Pharmacol.* 23:439-446 (1974).
Joy et al., "Marijuana and Medicine, Assessing the Science Base," Institute of Medicine, National Academy Press (ISBN: 0-309-51408-8) (1999).
Khan, "Formulation ID: JA7/286B1; Formulation Name: Nushka-e-Qutoor," Muheet-e-Azam, Matba Nizami, Kanpur, vol. III, p. 147 (1887) (Exhibit 5 of the Third Party Observation (Ref. C20)).
Khan, "Formulation ID: JA7/286D; Formulation Name: Marookh Bara-e- Warame-sulb," Muheet-e-Azam, Matba Nizami, Kanpur, vol. III, p. 147 (1887) (Exhibit 4 of the Third Party Observation (Ref. C20)).
Khan, "Formulation ID: FA1/29A; Formulation Name: Gaanja," vol. IV (Part 1), p. 15, Matba Nizami, Kanpur (1899) (Exhibit 2 of the Third Party Observation (Ref C20)).
Khan, "Formulation ID: JA6/480; Formulation Name: Ganja," Khazaain-al-Advia, Nadeem Yunus Printer/Sheikh Mohd Basheer & Sons, Lahore, vol. III., pp. 518-519 (1926) (Exhibit 6 of the Third Party Observation (Ref. C20)).
Langer et al., "Chemical and Physical Structure of Polymers as Carriers for Controlled Release of Bioactive Agents: A Review," *J. Macramol. Sci. Rev. Macromol. Chem.* C23(1):61-126 (1983).
Langer, "New Methods of Drug Delivery," *Science* 249:1527-1533 (1990).
Lee et al., "Controlled-Release Drug-Delivery Systems," in *Remington: The Science and Practice of Pharmacy*, 20th ed. Ch. 47, pp. 903-929, A.R. Gennaro (ed.), Lippincott (2000).
Lehmann et al., "A New Chromatography Method for the Isolation of (−)-$\Delta^9$-(trans)-Tetrahydrocannabinolic Acid A," *Phytochemical Anal.* 3:88-90 (1992).
Levin et al., "Resolution of chiral cannabinoids on amylase tris (3,5-dimethylphenylcarbamate) chiral stationary phase: Effects of structural features and mobile phase additives," *J. Chromatography A* 654:53-64 (1993).
Levy et al., "Inhibition of Calcification of Bioprosthetic Heart Valves by Local Controlled-Release Diphosphonate," *Science* 228:190-192 (1985).

(56) References Cited

OTHER PUBLICATIONS

Lipparini et al., "A Neuropharmacological Investigation of Some Trans-tetrahydrocannabinol Derivatives," *Physiol. Behavior* 4:527-532 (1969).

Lo et al., "Extraction," *Kirk-Othmer Encyclo. Chem. Technol.*, 4th ed. 10:125-180 (1993).

Lopez-Berestein, "Treatment of Systemic Fungal Infections with Liposomal-Amphotericin B," *Liposomes in the Therapy of Infectious Disease and Cancer*, pp. 317-327 (1989).

"Marinol," pp. 1846-1847 in *Physicians' Desk Reference*, 42nd Ed. (Medical Economics Co., Oradell, NJ, 1988).

"Marinol," in FDA *Orange Book*, pp. 3-14 (2004).

Martin et al., "Behavioral Comparisons of the Stereoisomers of Tetrahydrocannabinols," *Life Sci.* 29:565-574 (1981).

Mechoulam et al., "A Total Synthesis of $dl$-$\Delta^1$-Tetrahydrocannabinol, the Active Consituent of Hashish," *JACS Communications to the Editor* 87(14):3273-3275 (1965).

Mechoulam et al., "Stereospecific synthesis of (−)-$\Delta$-(1)- and (−)-$\Delta$-1-(6)-tetrahydrocannabinols," *JACS* 89(17):4552-4554 (1967).

Mechoulam et al., "Syntheses of $\Delta$-1-tetrahydrocannabinol and related cannabinoids," *JACS* 94(17):6159-6165 (1972).

Mechoulam et al., "A Random Walk Through a Cannabis Field," *Pharmacol. Biochem. Behavior* 40:461-464 (1991).

"Megestrol is Superior to Dronabinol," *Medical Advances, Medical Economic News*, p. 8 (Mar. 8, 2002).

Noyes et al., "Psychologic Effects of Oral Delta-9-tetrahydrocannabinol in Advanced Cancer Patients," *Comprehensive Psychiatry* 17(5):641-646 (1976).

O'Connor et al., "Powders," in *Remington: The Science and Practice of Pharmacy*, 19th ed. vol. 2, pp. 1598-1604, A.R. Gennaro (ed.), Mack Publishing (1995).

O'Connor et al., "Powders" in *Remington: The Science and Practice of Pharmacy*, 20th ed. Ch. 37, pp. 681-699, A.R. Gennaro (ed.), Lippincott (2000).

Office Communication for U.S. Appl. No. 11/455,256 mailed Jan. 8, 2010.

Office Communication for U.S. Appl. No. 11/455,256 mailed Sep. 30, 2010.

Office Communication for U.S. Appl. No. 11/455,256 mailed Jun. 17, 2011.

Office Communication for U.S. Appl. No. 11/455,256 mailed Apr. 14, 2014.

Petrzilka et al., "222. Uber Inhaltsstoffe des Haschisch—Umwandlung von (−)-$\Delta^{6,1}$-3,4-trans-Tetrahydrocannabinol in (−)-$\Delta^{1,2}$-3,4-trans-Tetrahydrocannabinol," *Helvetica Chimica ACTA* 50(7):2111-2113 (1967).

Petrzilka et al., "123. Synthese von Haschisch-Inhaltsstoffen," *Helvetica Chimica ACTA* 52(4):1102-1134 (1969)

Porter, "Coating of Pharmaceutical Dosage Forms," in *Remington: The Science and Practice of Pharmacy*, 20th ed. Ch. 46, pp. 894-902, A.R. Gennaro (ed.), Lippincott (2000).

Poster et al., "$\Delta^9$-Tetrahydrocannabinol in Clinical Oncology," *JAMA* 245(20):2047 (1981).

Razdan et al., "Hashish. X. Simple one-step synthesis of (−)-$\Delta$-1-tetrahydrocannabinol (THC) from $p$-mentha-2,8-dien-1-ol and olivetol," *JACS* 96(18):5860-5865 (1974).

Razdan et al., "A One-Step Synthesis of (−)-$\Delta^1$-Tetrahydrocannabinol from Chrysanthenol," *Experentia* 31(1):16-17 (1975).

Regelson et al., "Delta-9-tetrahydrocannabinol as an effective antidepressant and appetite-stimulating agent in advanced cancer patients," pp. 763-776 in *Pharmacology of Marihuana*, vol. 2, Braude & Szara, eds. (Raven Press, Ny, 1976).

Reichman et al., "$\Delta^9$-Tetrahydrocannabinol Increases Arachidonic Acid Levels in Guinea Pig Cerebral Cortex Slices," *Mol. Pharmacol.* 34:823-828 (1988).

Reichman et al., "$\Delta^9$-Tetrahydrocannabinol Inhibits Arachidonic Acid Acylation of Phospholipids and Triacylglycerols in Guinea Pig Cere bral Cortex Slices," *Mol. Pharmacol.* 40:547-555 (1991).

Rinaldi-Carmona et al., "SR 144528, the First Potent and Selective Antagonist of the CB2 Cannabinoid Receptor," *J. Pharmaco. Exper. Therapeutics* 284(2):644-650 (1998).

Roth, "Stereospecific presynaptic inhibitory effect of $\Delta^9$-tetrahydrocannabinol on cholinergic transmission in the myenteric plexus of the guinea pig," *Can. J. Physiol. Pharmacol.* 56:968-975 (1978).

Rudnic et al., "Oral Solid Dosage Forms," in *Remington: The Science and Practice of Pharmacy*, 20th ed. Ch. 45, pp. 858-893, A.R. Gennaro (ed.), Lippincott (2000).

Sadanandasarma et al., "Formulation ID: AK1/758; Formulation Name: Suddha Bhanga Visista Gunah Aur Matra," Kasinathsastri, ed., 11th Ed., pp. 720-723 (1979 (Reprinted-Delhi, 2000)) (Exhibit 1 of the Third Party Observation (Ref. C20)).

Sallan et al., "Antiemetics in Patients Receiving Chemotherapy for Cancer," *New England J. Med.* 302(3):135 (1980).

Saudek et al., "A Preliminary Trial of the Programmable Implantable Medication System for Insulin Delivery," *New England J. Med.* 321:574-579 (1989).

Scheckel et al., "Behavioral Effects in Monkeys of Racemates of Two Biologically Active Marijuana Constituents," *Science* 160:1467-1469 (1968).

Sciarra et al., "Aerosols," in *Remington: The Science and Practice of Pharmacy*, 20th ed. Ch. 50, pp. 963-979, A.R. Gennaro (ed.), Lippincott (2000).

Sefton, "Implantable Pumps," *CRC Crit. Rev. Biomed Eng.* 14:201-240 (1987).

Shire et al., "Structural Features of the Central Cannabinoid CB1 Receptor Involved in the Binding of the Specific CB1 Antagonist SR 141716A," *J. Biol. Chem.* 271(12):6941-6946 (1996).

Shoyama et al., "Cannabis. XV. Preparation and Stability of Delta$^9$-Tetrahydrocannabinol-Beta-Cyclodextrin Inclusion Complex," *J. Natural Products* 46(5):633-637 (1983).

Singhal et al., "Drug Polymorphism and Dosage Form Design: A Practical Perspective," *Adv. Drug Deliv. Rev.* 56:335-347 (2004).

Taylor et al., "Active Constituents of Hashish. Synthesis of dl-$\Delta$-3,4-trans-Tetrahydrocannabinol," *JACS* 88(2):367-369 (2002).

Treat et al., "Liposome encapsulated doxorubicin—preliminary results of phase I and phase II trials" *Liposomes in the Theraoy of Infectious Disease and Cancer*, pp. 317-327 and 353-365 (1989).

Turk et al., "The identification, isolation, and preservation of $\Delta^9$-tetrahydrocannabinol ($\Delta^9$-THC)," *J. Pharm. Pharmac.* 23:190-195 (1971).

Ungerleider et al., "Cannabis and cancer chemotherapy. A comparison of oral delta-9-THC and prochlorperazine," *Cancer* 50(4):636-645 (1982).

Vippagunta et al., "Crystalline solids," *Adv. Drug Delivery Rev's* 48:3-26 (2001).

Wadleigh et al., "Dronabinol enhancement of appetite in cancer patients" *Proc. Amer. Soc. Clinical Oncology*, p. 331 (Mar. 1990).

Wise, ed., *Handbook of Pharmaceutical Controlled Release Technology* (Marcel Dekker, Inc., NY, 2000).

"Workshop on the Medical Utility of Marijuana," Web Reference: National Institutes of Health, http://www.nih.gov/news/medmarijuana/MedicalMarijuana.htm (1997) (last accessed Jun. 24, 2010).

Written Opinion of the International Searching Authority for PCT/EP2005/012378 date-stamped Feb. 28, 2006.

Written Opinion of the International Searching Authority for PCT/EP2006/005761 dated Dec. 16, 2007.

\* cited by examiner

METHODS FOR PURIFYING TRANS-(−)-Δ⁹-TETRAHYDROCANNABINOL AND TRANS-(+)-Δ⁹-TETRAHYDROCANNABINOL

CROSS REFERENCE TO RELATED APPLICATIONS

This application is a divisional of application Ser. No. 13/774,955, filed Feb. 22, 2013, which is a continuation of application Ser. No. 11/791,415, filed Aug. 12, 2009, now U.S. Pat. No. 8,383,842, which is a national stage of International application serial no. PCT/EP2005/012378, filed Nov. 18, 2005, which claims the benefit, under 35 U.S.C. §119(e), of provisional application No. 60/630,556, filed Nov. 22, 2004, the contents of all of which are incorporated herein by reference.

1. FIELD OF THE INVENTION

The present invention relates to methods for purifying trans-(−)-Δ$^9$-tetrahydrocannabinol or trans-(+)-Δ$^9$-tetrahydrocannabinol; compositions comprising purified forms of trans-(−)-Δ$^9$-tetrahydrocannabinol or trans-(+)-Δ$^9$-tetrahydrocannabinol; and methods for treating or preventing a condition such as pain, emesis, loss of appetite or weight loss comprising administering purified form of trans-(−)-Δ$^9$-tetrahydrocannabinol to a patient in need thereof.

2. BACKGROUND OF THE INVENTION (−)-6a,10a-Trans-Δ$^9$-tetrahydrocannabinol ("(−)-Δ$^9$-THC") is mainly responsible for the antiemetic effects associated with *cannabis* (S. E. Sallen et al., *N. Engl. J. Med.* 302:135 (1980); A. E. Chang et al., *Cancer* 47:1746 (1981); and D. S. Poster et al., *J. Am. Med. Asso.* 245:2047 (1981)). Both trans-(−)-Δ$^9$-THC and trans-(+)-Δ$^9$-THC, the trans-(−)- and (+)-enantiomers, respectively, of (−)-Δ$^9$-THC, are reported to be useful for treating pain, with trans-(−)-Δ$^9$-THC reported to be more potent than trans-(+)-Δ$^9$-THC (see, e.g., G. Jones et al., *Biochem. Pharmacol.* 23:439 (1974); S. H. Roth, *Can. J. Physiol. Pharmacol.* 56:968 (1978); B. R. Martin et al., *Life Sciences* 29:565 (1981); M. Reichman et al., *Mol. Pharmacol.* 34:823 (1988); and M. Reichman et al., *Mol. Pharmacol.* 40:547 (1991)). trans-(−)-Δ$^9$-THC is reported to be useful an antiemetic to relieve nausea and vomiting in patients receiving cancer chemotherapy and to stimulate weight gain in patients suffering from symptomatic HIV infection (see U.S. Pat. No. 6,703,418 B2 to Plasse). An encapsulated formulation of synthetic trans-(−)-Δ$^9$-THC ("dronabinol") in sesame oil is currently sold as Marinol® by Unimed Pharmaceuticals, Inc., in 2.5, 5, and 10 mg dosage strengths.

Trans-(−)-Δ$^9$-THC can be extracted from hashish (see, Y. Gaoni et al., *J. Am. Chem. Soc.* 93:217 (1971); and U.S. Pat. No. 6,365,416 B1 to Elsohly et al.). The concentration of trans-(−)-Δ$^9$-THC in hashish, however, ranges from only about 1-5% depending on the source, and, even after extraction, trans-(−)-Δ$^9$-THC must be separated from other impurities such as cannabinoid isomers.

R. F. Turk et al., *J. Pharm. Pharmac.* 23:190-195 (1971) describes a method for isolating trans-(−)-Δ$^9$-THC from marihuana, but the product contained an undetermined amount of carboxylic precursors of THC.

The following paragraphs relate to known methods that purport making trans-(−)-Δ$^9$-THC or (±)-Δ$^9$-THC:

U.S. Pat. No. 3,560,528 to Petrizilka describes the reaction of (+)-p-mentha-2,8-dien-1-ol with olivetol in the presence of p-toluenesulfonic acid monohydrate ("PTSA.H$_2$O") or trifluoroacetic acid in refluxing benzene to provide (−)-Δ$^8$-THC, which can be converted to trans-(−)-Δ$^9$-THC by addition of HCl followed by dehydrochlorination (see Y. Mechoulam et al., *J. Am. Chem. Soc.* 89:4553 (1967); and R. Mechoulam et al., *J. Am. Chem. Soc.* 94:6159 (1972)).

U.S. Pat. No. 4,025,516 to Razdan et al. describes the reaction of a mixture of cis/trans-(+)-p-mentha-2,8-dien-1-ol with olivetol in an inert organic solvent in the presence of an excess of a non-alkaline dehydrating agent and an acid catalyst to form trans-(−)-Δ$^9$-THC; this patent also describes the reaction of (−)-cannabidiol ("(−)-CBD") or (−)-abnormal-CBD ("(−)-abn-CBD") with a Lewis acid such as boron trifluoride diethylether ("BF$_3$.Et$_2$O") in an inert solvent under anhydrous conditions to form trans-(−)-Δ$^9$-THC.

R. K. Razdan et al., *J. Am. Chem. Soc.* 96:5860 (1974) describes the reaction of a mixture of cis/trans-(+)-p-mentha-2,8-dien-1-ol with olivetol in the presence of 1% BF$_3$.Et$_2$O, methylene chloride and anhydrous magnesium sulfate to form trans-(−)-Δ$^9$-THC.

U.S. Pat. No. 4,381,399 to Olsen et al. describes a method for separating trans-(−)-Δ$^9$-THC from a crude synthetic mixture, the method comprising esterifying the crude mixture, isolating the resultant trans-(−)-Δ$^9$-THC ester, hydrolyzing the ester, and distilling trans-(−)-Δ$^9$-THC at reduced pressure.

K. E. Fahrenholtz et al., *J. Am. Chem. Soc.* 89:5934-5941 (1967) describes the hydrolysis of (±)-1-m-nitrobenzenesulfoanate-6a,10a-trans-Δ$^9$-tetrahydrocannabinol with NaOH in aqueous methanol to provide (±)-Δ$^9$-THC, which was subsequently crystallized from hexane.

E. G. Taylor et al., *J. Am. Chem. Soc.* 88:367 (1966) describes the reaction of citral with olivetol in acidified ethanol to form (±)-Δ$^9$-THC in about 35% yield.

S. L. Levin et al., *J. Chromatogr. A* 654:53-64 (1993) describe a method for resolving trans-(−)-Δ$^9$-THC and trans-(+)-Δ$^9$-THC from a composition comprising equimolar amounts of the trans-(−)- and (+)-enantiomer.

Despite these described methods, there remains a need for improved methods for making trans-(−)-Δ$^9$-THC in pure or substantially pure form.

Citation of any reference in Section 2 of this application is not an admission that the reference is prior art to the application.

3. SUMMARY OF THE INVENTION

The invention relates to methods for preparing a composition comprising trans-(−)-Δ$^9$-THC or trans-(+)-Δ$^9$-THC.

In one embodiment, the invention relates to a method for preparing a composition comprising at least about 98% by weight of trans-(−)-Δ$^9$-THC based on the total amount of cannabinoids.

In another embodiment, the invention relates to a method for preparing a composition comprising trans-(−)-Δ$^9$-THC, comprising:

allowing a composition comprising (±)-Δ$^9$-THC and an eluting solvent to separate on a chiral stationary phase to provide a trans-(−)-Δ$^9$-THC composition, wherein the (±)-Δ$^9$-THC is obtained from crystalline (±)-Δ$^9$-THC.

In another embodiment, the invention relates to a method for preparing a trans-(−)-Δ$^9$-THC composition, comprising:

allowing a composition comprising (±)-Δ$^9$-THC and an eluting solvent to separate on a chiral stationary phase to provide a trans-(−)-Δ$^9$-THC composition comprising at least about 98% by weight of trans-(−)-Δ$^9$-THC based on the total amount of
trans-(−)-Δ$^9$-THC and trans-(+)-Δ$^9$-THC;

wherein the (±)-Δ⁹-THC was obtained by allowing trans-(−)-Δ⁹-THC and trans-(+)-Δ⁹-THC to crystallize from a first composition comprising trans-(−)-Δ⁹-THC, trans-(+)-Δ⁹-THC, and a non-polar organic solvent to provide crystalline (±)-Δ⁹-THC and a liquid phase.

The invention also relates to methods for preparing a composition comprising at least about 98% by weight of trans-(+)-Δ⁹-THC based on the total amount of cannabinoids.

In one embodiment, the invention relates to a method for preparing a composition comprising trans-(+)-Δ⁹-THC, comprising:

allowing a composition comprising (±)-Δ⁹-THC and an eluting solvent to separate on a chiral stationary phase to provide a trans-(+)-Δ⁹-THC composition, wherein the (±)-Δ⁹-THC is obtained from crystalline (±)-Δ⁹-THC.

In another embodiment, the invention relates to a method for preparing a trans-(+)-Δ⁹-THC composition, comprising:

allowing a composition comprising (±)-Δ⁹-THC and an eluting solvent to separate on a chiral stationary phase to provide a trans-(+)-Δ⁹-THC composition comprising at least about 98% by weight of the trans-(+)-Δ⁹-THC based on the total amount of the trans-(+)-Δ⁹-THC and trans-(−)-Δ⁹-THC;

wherein the (±)-Δ⁹-THC was obtained by allowing trans-(−)-Δ⁹-THC and trans-(+)-Δ⁹-THC to crystallize from a first composition comprising trans-(−)-Δ⁹-THC, trans-(+)-Δ⁹-THC, and a non-polar organic solvent to provide crystalline (±)-Δ⁹-THC and a liquid phase.

The invention also relates to compositions comprising either trans-(−)-Δ⁹-THC or trans-(+)-Δ⁹-THC.

In one embodiment, the invention relates to a composition comprising at least 99.0% by weight of trans-(−)-Δ⁹-THC based on the total amount of cannabinoids.

In another embodiment, the invention relates to a composition comprising at least 99.0% by weight of trans-(+)-Δ⁹-THC based on the total amount of cannabinoids.

The invention also relates to pharmaceutical compositions comprising trans-(−)-Δ⁹-THC. In one embodiment, the invention relates to pharmaceutical compositions comprising at least 99.0% by weight of trans-(−)-Δ⁹-THC based on the total amount of cannabinoids.

The invention still further relates to methods for treating or preventing a condition such as, e.g., emesis, loss of weight or loss of appetite comprising administering to a patient in need thereof an effective amount of a composition comprising at least 99.0% by weight of trans-(−)-Δ⁹-THC based on the total amount of cannabinoids.

The present invention can be understood more fully by reference to the following detailed description and illustrative examples, which exemplify non-limiting embodiments of the invention.

4. DETAILED DESCRIPTION OF THE INVENTION

4.1. Definitions

As used herein, the generic term "Δ⁹-THC" refers to trans-(−)-Δ⁹-THC, trans-(+)-Δ⁹-THC, (±)-Δ⁹-THC, or any mixture thereof.

trans-(−)-Δ⁹-THC has the structure of formula (1a):

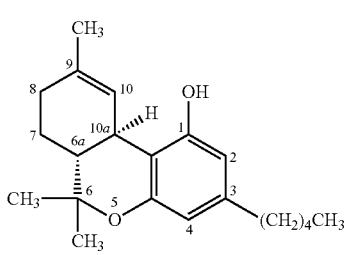

(1a)

Trans-(+)-Δ⁹-THC has the structure of (1b):

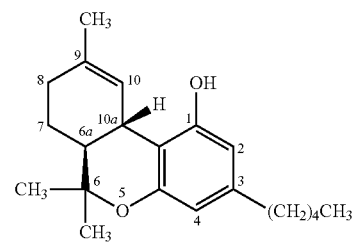

(1b)

As used herein, the generic term "Δ⁸-THC" refers to (−)-Δ⁸-THC, (+)-Δ⁸-THC, (±)-Δ⁸-THC, or any mixture thereof.

(−)-Δ⁸-THC has the structure of formula (2a):

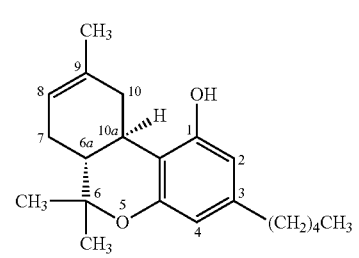

(2a)

(−)-Δ⁸-THC has the structure of formula (3a):

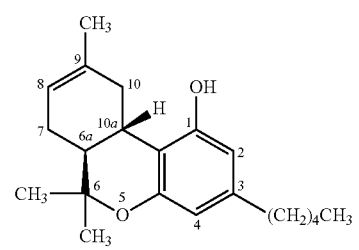

(2b)

As used herein, the generic term "CBD" refers to (−)-CBD, (+)-CBD, (±)-CBD, or any mixture thereof.

(−)-CBD has the structure of formula (3a):

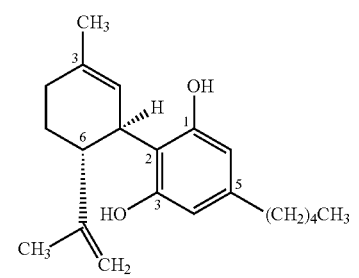

(3a)

(+)-CBD has the structure of formula (3b):

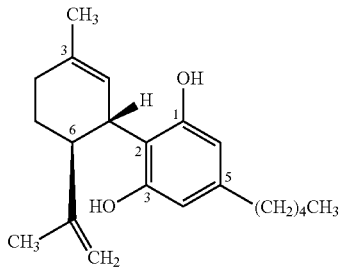
(3b)

As used herein, the generic term "CBD-bis-1,3-(3,5-dinitrobenzoate)" refers to (−)-CBD-bis(3,5-dinitrobenzoate), (+)-CBD-bis(3,5-dinitrobenzoate), (±)-CBD-bis(3,5-dinitrobenzoate), or any mixture thereof.

(−)-CBD-bis(3,5-dinitrobenzoate) has the structure of formula (4a):

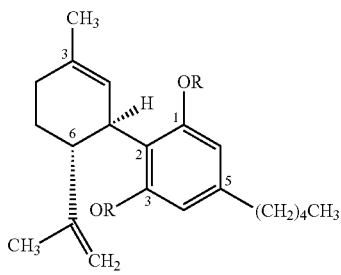
(4a)

where R is —C(O)(3,5-$C_6H_3(NO_2)_2$).

(+)-CBD-bis(3,5-dinitrobenzoate) has the structure of formula (4b):

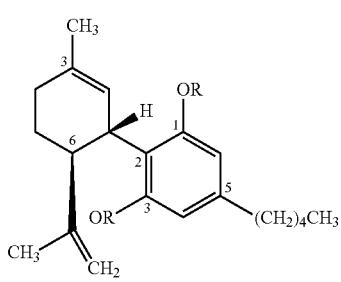
(4b)

where R is —C(O)(3,5-$C_6H_3(NO_2)_2$).

As used herein, the generic term "trans-$\Delta^9$-THC carboxylic acid" refers to trans-(−)-$\Delta^9$-THC carboxylic acid, trans-(+)-$\Delta^9$-THC carboxylic acid, trans-(±)-$\Delta^9$-THC carboxylic acid, or any mixture thereof trans-(−)-$\Delta^9$-THC carboxylic acid has the structure of formula (5a):

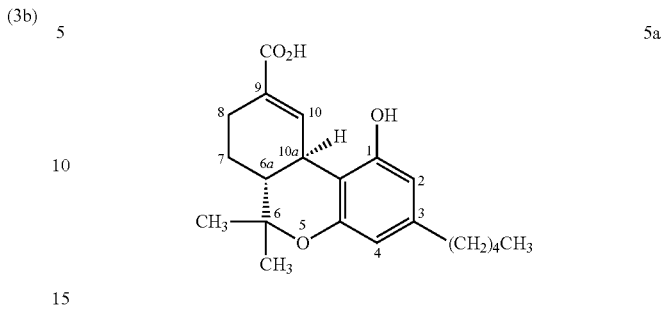
(5a)

trans-(+)-$\Delta^9$-THC carboxylic acid has the structure of formula (5b):

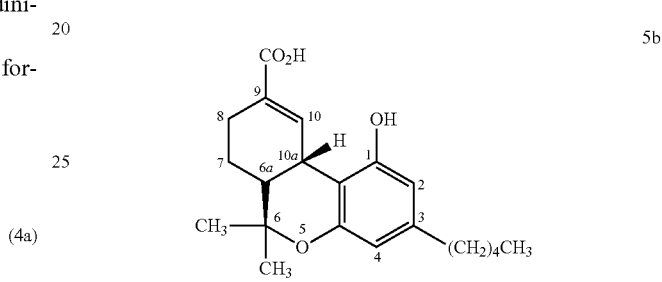
(5b)

The term "halide" refers to fluoride, chloride, bromide or iodide.

The term "-halo" means —F, —Cl, —Br or —I.

The term "—($C_1$-$C_4$)alkyl" means a saturated straight-chain or branched hydrocarbon having from 1 to 4 carbon atoms. Representative saturated straight chain ($C_1$-$C_4$)alkyls are -methyl, -ethyl, -n-propyl, and -n-butyl. Representative saturated branched —($C_1$-$C_4$)alkyls are -isopropyl, -sec-butyl, -isobutyl, and -tert butyl.

The phrase "anhydrous organic solvent," unless otherwise defined herein, means an organic solvent having an amount of water that is less than about 0.01% by weight of the total amount of water and organic solvent.

The term "cannabinoids" refers to $\Delta^9$-THC including trans-$\Delta^9$-THC and cis-$\Delta^9$-THC; structural isomers of $\Delta^9$-THC having a molecular formula $C_{21}H_{30}O_2$, including $\Delta^8$-THC, (−)-$\Delta^8$-iso-THC, and (+)-$\Delta^8$-iso-THC; cannabinol and structural isomers of cannabinol having a molecular formula of $C_{21}H_{28}O_2$; $\Delta^9$-THC-carboxylic acid; $\Delta^9$-THC precursors including CBD, abn-CBD, (+)-abn-CBD, olivetol, (+)-p-mentha-2,8-dien-1-ol and (−)-p-mentha-2,8-dien-1-ol; salts thereof; and derivatives thereof including acids, ethers, esters, amines, and the like.

Unless otherwise specified herein, the phrase "cannabinoid impurities" means cannabinoids other than trans-(−)-$\Delta^9$-THC or trans-(+)-$\Delta^9$-THC.

Unless otherwise specified herein, the generic term "$\Delta^9$-THC-carboxylic acid" means (−)-$\Delta^9$-THC-carboxylic acid, (+)-$\Delta^9$-THC-carboxylic acid, or (±)-THC-carboxylic acid.

As used herein, the phrase "crystalline (±)-$\Delta^9$-THC" means a solid form of $\Delta^9$-THC comprising about equimolar amounts of trans-(−)-$\Delta^9$-THC and trans-(+)-$\Delta^9$-THC and having an amount of trans-(−)-$\Delta^9$-THC and trans-(+)-$\Delta^9$-THC that is at least about 95% by weight based on the total weight of cannabinoids. As used herein, the term "patient" means an animal, including, but not limited, to an animal such a cow, horse, sheep, pig, chicken, turkey, quail, cat, dog, mouse, rat, rabbit, guinea pig, etc., and is more preferably a mammal, and most preferably a human

4.2. Methods for Purifying trans-(−)-$\Delta^9$-THC

As noted above, the present invention relates methods for making compositions comprising at least about 98% by weight of trans-(−)-$\Delta^9$-THC or trans-(+)-$\Delta^9$-THC based on the total amount of cannabinoids.

In one embodiment, the invention relates to a method comprising allowing a composition comprising (±)-$\Delta^9$-THC and an eluting solvent to separate on a chiral stationary phase to provide a trans-(−)-$\Delta^9$-THC or trans-(+)-$\Delta^9$-THC composition, wherein the (±)-$\Delta^9$-THC is obtained from crystalline (±)-$\Delta^9$-THC. Without being limited by theory, Applicants believe that cannabinoid impurities typically present in $\Delta^9$-THC compositions are substantially, if not completely, removed when trans-(−)-$\Delta^9$-THC and trans-(+)-$\Delta^9$-THC are allowed to form crystalline (±)-$\Delta^9$-THC. Subsequent resolution of (±)-$\Delta^9$-THC obtained from crystalline (±)-$\Delta^9$-THC with an eluting solvent on a chiral stationary phase provides a composition comprising at least about 98% by weight of trans-(−)-$\Delta^9$-THC or trans-(+)-$\Delta^9$-THC based on the total amount of cannabinoids.

In one embodiment, the invention relates to a method for preparing a composition comprising trans-(−)-$\Delta^9$-THC, comprising:

allowing a composition comprising (±)-$\Delta^9$-THC and an eluting solvent to separate on a chiral stationary phase to provide a trans-(−)-$\Delta^9$-THC composition, wherein the (±)-$\Delta^9$-THC is obtained from crystalline (±)-$\Delta^9$-THC.

In another embodiment, the invention relates to a method for preparing a composition comprising trans-(+)-$\Delta^9$-THC, comprising:

allowing a composition comprising (±)-$\Delta^9$-THC and an eluting solvent to separate on a chiral stationary phase to provide a trans-(+)-$\Delta^9$-THC composition, wherein the (±)-$\Delta^9$-THC is obtained from crystalline (±)-$\Delta^9$-THC.

Crystalline (±)-$\Delta^9$-THC useful in the present invention can be obtained by any known or later-developed method. For example, a non-limiting method for obtaining crystalline (±)-$\Delta^9$-THC includes crystallization from a first composition comprising trans-(−)-$\Delta^9$-THC, trans-(+)-$\Delta^9$-THC, and a non-polar organic solvent to provide crystalline (±)-$\Delta^9$-THC as described below in Section 4.3.

In another embodiment, the invention relates to a method for preparing a trans-(−)-$\Delta^9$-THC composition, comprising:

allowing a composition comprising (±)-$\Delta^9$-THC and an eluting solvent to separate on a chiral stationary phase to provide a trans-(−)-$\Delta^9$-THC composition comprising at least about 98% by weight of trans-(−)-$\Delta^9$-THC based on the total amount of trans-(−)-$\Delta^9$-THC and trans-(+)-$\Delta^9$-THC;

wherein the (±)-$\Delta^9$-THC was obtained by allowing trans-(−)-$\Delta^9$-THC and trans-(+)-$\Delta^9$-THC to crystallize from a first composition comprising trans-(−)-$\Delta^9$-THC, trans-(+)-$\Delta^9$-THC, and a non-polar organic solvent to provide crystalline (±)-$\Delta^9$-THC and a liquid phase.

In another embodiment, the invention relates to a method for preparing a trans-(+)-$\Delta^9$-THC composition, comprising:

allowing a composition comprising (±)-$\Delta^9$-THC and an eluting solvent to separate on a chiral stationary phase to provide a trans-(+)-$\Delta^9$-THC composition comprising at least about 98% by weight of trans-(+)-$\Delta^9$-THC based on the total amount of trans-(+)-$\Delta^9$-THC and trans-(−)-$\Delta^9$-THC;

wherein the (±)-$\Delta^9$-THC was obtained by allowing trans-(−)-$\Delta^9$-THC and trans-(+)-$\Delta^9$-THC to crystallize from a first composition comprising trans-(−)-$\Delta^9$-THC, trans-(+)-$\Delta^9$-THC, and a non-polar organic solvent to provide crystalline (±)-$\Delta^9$-THC and a liquid phase.

Compositions comprising trans-(−)-$\Delta^9$-THC and trans-(+)-$\Delta^9$-THC useful for obtaining crystalline (±)-$\Delta^9$-THC can be obtained by methods described in Section 4.3.

4.3. The Crystallizing Step

As noted above, crystalline (±)-$\Delta^9$-THC can, in one embodiment, be obtained by allowing trans-(−)-$\Delta^9$-THC and trans-(+)-$\Delta^9$-THC to crystallize from a composition comprising trans-(−)-$\Delta^9$-THC, trans-(+)-$\Delta^9$-THC and a non-polar organic solvent (the "Crystallizing Step") to provide crystalline (±)-$\Delta^9$-THC and a liquid phase. Compositions comprising trans-(−)-$\Delta^9$-THC, trans-(+)-$\Delta^9$-THC and a non-polar organic solvent useful for the Crystallizing Step can be obtained by any known or later-developed method.

For example, crystalline (±)-$\Delta^9$-THC can be obtained by contacting a suitable amount of trans-(−)-$\Delta^9$-THC and trans-(+)-$\Delta^9$-THC with a non-polar organic solvent. The order and rate of addition of the trans-(−)-$\Delta^9$-THC, the trans-(+)-$\Delta^9$-THC and the non-polar organic solvent is not critical and can be carried out sequentially or substantially simultaneously. As an example, trans-(−)-$\Delta^9$-THC, optionally in the presence of a non-polar organic solvent, and trans-(+)-$\Delta^9$-THC, optionally in the presence of a non-polar organic solvent, can be added to a non-polar organic solvent. Likewise, trans-(+)-$\Delta^9$-THC in the presence of a non-polar organic solvent and trans-(−)-$\Delta^9$-THC in the presence of a non-polar organic solvent can be admixed.

Trans-(−)-$\Delta^9$-THC can be obtained from natural products or by synthetic methods. In one embodiment, trans-(−)-$\Delta^9$-THC is obtained from a natural product such as, e.g., hashish or marijuana (see Y. Gaoni et al., *J. Am. Chem. Soc.* 93:217 (1971); and U.S. Pat. No. 6,365,416 B1 to Elsohly et al.).

Trans-(−)-$\Delta^9$-THC can also be obtained by known synthetic methods including, but not limited to, reaction of a cis/trans mixture of (+)-p-mentha-2,8-dien-1-ol with olivetol in the presence of an acid catalyst such a para-toluenesulfonic acid and a dehydrating agent (see U.S. Pat. No. 3,560,528 to Petrizilka and U.S. Pat. No. 4,025,516 to Razdan et al.); reaction of (−)-CBD with a Lewis acid such as $BF_3.Et_2O$ in an inert solvent under anhydrous conditions (see U.S. Pat. No. 4,025,516 to Razdan et al.; and International publication no. WO 02/070506); or reaction of (−)-$\Delta^8$-THC with HCl followed by dehydrochlorination (see Y. Mechoulam et al., *J. Am. Chem. Soc.* 89:4553 (1967); and R. Mechoulam et al., *J. Am. Chem. Soc.* 94:6159 (1972)). Alternatively, trans-(−)-$\Delta^9$-THC can be obtained by methods described in Section 5.

Trans-(+)-$\Delta^9$-THC, which is not known to occur in nature, can be made by known synthetic methods including, but not limited to, reaction of (+)-$\Delta^8$-THC with HCl followed by dehydrochlorination (see R. Mechoulam et al., *J. Am. Chem. Soc.* 94:6159 (1972). Alternatively, trans-(+)-$\Delta^9$-THC can be obtained by methods described in Section 5. In one embodiment, trans-(+)-$\Delta^9$-THC used in the Crystallizing Step is "recycled" from a previous resolution of (±)-$\Delta^9$-THC on a chiral stationary phase as described in Section 4.4

In another embodiment, the trans-(−)-$\Delta^9$-THC and trans-(+)-$\Delta^9$-THC used in the Crystallizing Step can be obtained as a mixture of enantiomers by a direct synthetic method. When a synthetic method is used, the ratio of trans-(−)-$\Delta^9$-THC and trans-(+)-$\Delta^9$-THC can vary depending on the optical purity of the reagents and the synthetic process. In one embodiment, trans-(−)-$\Delta^9$-THC and trans-(+)-$\Delta^9$-THC are obtained in about equimolar amounts by a synthetic route using racemic reagents. Non-limiting methods for preparing trans-(−)-$\Delta^9$-THC and trans-(+)-$\Delta^9$-THC by a direct synthetic route include reaction of citral and olivetol in the presence of a Lewis acid (see R. Mechoulam et al., *J. Am. Chem. Soc.* 94:6159 (1972)) or hydrolysis of (±)-1-m-nitrobenzene-sulfoanate-6a,10a-trans-$\Delta^9$-THC with NaOH in aqueous methanol (K. E. Fahrenholtz et al, *J. Am. Chem. Soc.* 89:5934-5941 (1967)). Alternatively, (±)-$\Delta^9$-THC can be obtained by methods described in Section 5.

In yet another embodiment, the trans-(−)-$\Delta^9$-THC and trans-(+)-$\Delta^9$-THC used in the Crystallizing Step can be obtained from derivatives of trans-(−)-$\Delta^9$-THC and trans-(+)-$\Delta^9$-THC. For example, an admixture of trans-(−)-$\Delta^9$-THC and trans-(+)-$\Delta^9$-THC can be reacted with a phenol protecting group such as m-nitrobenzenesulfonate and crystallized to provide 2-m-nitrobenzenesulfonate-(±)-$\Delta^9$-THC (see U.S. Pat. No. 3,507,885 to Fahrenholtz; and K. E. Fahrenholtz et al., *J. Am. Chem. Soc.* 89:5934-5491 (1967))). The 2-m-nitrobenzenesulfonate-(±)-$\Delta^9$-THC can then be deprotected, and the resultant composition comprising trans-(−)-$\Delta^9$-THC and trans-(+)-$\Delta^9$-THC can be crystallized from a composition comprising the trans-(−)-$\Delta^9$-THC, the trans-(+)-$\Delta^9$-THC, and a non-polar organic solvent to provide crystalline (±)-$\Delta^9$-THC.

The ratio of trans-(−)-$\Delta^9$-THC and trans-(+)-$\Delta^9$-THC used in the Crystallizing Step can vary. In one embodiment, the trans-(−)-$\Delta^9$-THC is present in an amount from about 0.75 to about 1.25 molar equivalents per molar equivalent of trans-(+)-$\Delta^9$-THC. In another embodiment, the trans-(−)-$\Delta^9$-THC is present in an amount from about 0.9 to about 1.1 molar equivalents per molar equivalent of trans-(+)-$\Delta^9$-THC. In another embodiment, the trans-(−)-$\Delta^9$-THC is present in an amount from about 0.95 to about 1.05 molar equivalents per molar equivalent of trans-(+)-$\Delta^9$-THC. And in another embodiment, the trans-(−)-$\Delta^9$-THC is present in an amount of about 1 molar equivalent per molar equivalent of trans-(+)-$\Delta^9$-THC.

Non-limiting examples of non-polar organic solvents that are useful in the Crystallizing Step include aliphatic ($C_4$-$C_{10}$) hydrocarbons such as butane, pentane, hexane, heptane, octane, nonane, decane, including straight-chained aliphatic hydrocarbons, branched aliphatic hydrocarbons and cyclic aliphatic hydrocarbons, or any mixture thereof.

In one embodiment, the non-polar organic solvent used in the Crystallizing Step is a straight-chain or branch-chain heptane. In another embodiment, the non-polar organic solvent used in the Crystallizing Step is pentane, hexane, heptane, octane or isooctane. In another embodiment, the non-polar organic solvent used in the Crystallizing Step is n-heptane.

The amount of the non-polar organic solvent used in the Crystallizing Step can vary and will depend, in part, on the amount and type of cannabinoid impurities and temperature. Typically, the non-polar organic solvent is present in an amount sufficient to provide a mixture having a $\Delta^9$-THC concentration from about 1% to about 95%, preferably from about 20% to about 75%, more preferably from about 40% to about 60% by weight based on the total amount of $\Delta^9$-THC and the non-polar organic solvent.

The Crystallizing Step is carried out for a time and at a temperature sufficient to provide (±)-$\Delta^9$-THC crystals. A time sufficient to crystallize (±)-$\Delta^9$-THC is from about 1 hour to about 200 hours; in another embodiment, from about 5 hours to about 150 hours; in another embodiment, from about 25 hours to about 100 hours; and in another embodiment, from about 30 hours to about 75 hours.

Typically, a temperature sufficient to provide crystalline (±)-$\Delta^9$-THC is from about −78° C. to about 100° C.; in another embodiment, from about −50° C. to about 25° C.; in another embodiment, from about −30° C. to about 0° C.; and in another embodiment, from about −25° C. to about −15° C.

In certain embodiments, the Crystallizing Step is carried out at two or more temperatures. In one embodiment, the composition comprising trans-(−)-$\Delta^9$-THC, trans-(+)-$\Delta^9$-THC and a non-polar organic solvent is prepared at a first temperature, e.g., 20° C. or higher. Without being limited by theory, Applicants believe that forming the composition at a temperature of 20° C. or higher increases the solubility of the trans-(−)-$\Delta^9$-THC and the trans-(+)-$\Delta^9$-THC in the non-polar organic solvent. The temperature of the admixture can then be decreased to a second temperature, e.g., 0° C. or lower. Without being limited by theory, Applicants believe that holding the admixture at a temperature of 0° C. or lower decreases the solubility of (±)-$\Delta^9$-THC and promotes crystallization. Optionally, the temperature of the admixture can be further decreased to third temperature, e.g., −20 to −15° C. As noted above, such a decrease in temperature is believed to enhance the (±)-$\Delta^9$-THC crystallization process.

In one embodiment, trans-(−)-$\Delta^9$-THC and trans-(+)-$\Delta^9$-THC are dissolved in a non-polar organic solvent; the resultant solution is cooled to about 0° C.; the resultant mixture is further cooled to about −15° C.; and the resultant crystalline (±)-$\Delta^9$-THC is separated from the liquid phase.

In another embodiment, the Crystallizing Step is carried out in the presence of a seed crystal. Typically, the seed crystal, when used, is added to the cold (e.g., 0° C. or lower) admixture comprising trans-(−)-$\Delta^9$-THC, trans-(+)-$\Delta^9$-THC and the non-polar organic solvent. In one embodiment, the seed crystal is (±)-$\Delta^9$-THC.

The progress of the Crystallizing Step can be monitored visually or using conventional analytical techniques, including, but not limited to, thin-layer chromatography ("TLC"), high-performance liquid chromatography ("HPLC"), gas chromatography ("GC"), gas-liquid chromatography ("GLC"), infrared spectroscopy ("IR"), Raman spectroscopy ("Raman") and nuclear magnetic resonance spectroscopy ("NMR") such as $^1$H or $^{13}$C NMR.

The Crystallizing Step can be carried out at reduced pressure, atmospheric pressure or elevated pressure. In one embodiment, the Crystallizing Step is carried out at atmospheric pressure.

In one embodiment, certain impurities are removed from the trans-(−)-$\Delta^9$-THC and/or trans-(+)-$\Delta^9$-THC compositions prior to carrying out the Crystallizing Step. Non-limiting methods for removing impurities prior to carrying out the Crystallizing Step include column chromatography (see Section 4.4) or extraction under basic conditions as described below.

In one embodiment, (+)-$\Delta^9$-THC, (−)-$\Delta^9$-THC, or (±)-$\Delta^9$-THC is contacted with base prior to carrying out the Crystallizing Step.

In another embodiment, the invention also relates to a method for purifying trans-(+)-$\Delta^9$-THC, trans-(−)-$\Delta^9$-THC, or trans-(±)-$\Delta^9$-THC (the "$\Delta^9$-THC Purification Method") comprising:

contacting trans-(+)-$\Delta^9$-THC, trans-(−)-$\Delta^9$-THC, or trans-(±)-$\Delta^9$-THC with a first water-immiscible organic solvent, a water-miscible alcohol, water, and an alkali metal hydroxide (the "Caustic Contacting Step") to form a biphasic mixture comprising (i) a first organic phase and (ii) an alcoholic-caustic phase comprising trans-(−)-$\Delta^9$-THC and trans-(+)-$\Delta^9$-THC.

Without being limited by theory, it is believed that the Caustic Contacting Step extracts impurities from the $\Delta^9$-THC-containing alcoholic-caustic phase into the first organic phase, which impurities may impede or prevent (±)-$\Delta^9$-THC from crystallizing from the composition comprising the trans-(−)-$\Delta^9$-THC, the trans-(+)-$\Delta^9$-THC, and the non-polar organic solvent.

The amount of alkali metal hydroxide used in the Caustic Contacting Step typically ranges from about 1 to about 1000 molar equivalents per molar equivalent of $\Delta^9$-THC; in another embodiment, the amount of alkali metal hydroxide ranges from about 10 to about 100 molar equivalents per molar equivalent of trans-$\Delta^9$-THC; and in another embodiment, amount of alkali metal hydroxide ranges from about 25 to about 55 molar equivalents per molar equivalent of trans-$\Delta^9$-THC.

Non-limiting examples of water-miscible alcohols useful in the Caustic Contacting Step include methanol, ethanol, isopropanol, or any combination thereof. In one embodiment, the water-miscible alcohol is methanol.

The amount of water-miscible alcohol used in the Caustic Contacting Step typically is from about 1 part to about 100 parts by weight based on the weight of the alkali metal hydroxide; in another embodiment, the amount of water-miscible alcohol is from about 1 part to about 25 parts by weight based on the weight of the alkali metal hydroxide; and in another embodiment, the amount of water-miscible alcohol is from about 5 parts to about 10 parts by weight based on the weight of the alkali metal hydroxide.

Non-limiting examples of first water-immiscible organic solvents useful in the Caustic Contacting Step include the non-polar organic solvents described above for the Crystallizing Step. In one embodiment, the first water-immiscible solvent is heptane.

The amount of first water-immiscible organic solvent used in the Caustic Contacting Step typically is from about 1 part to about 1000 parts by weight based on the weight of the $\Delta^9$-THC; in another embodiment, the amount of water-immiscible organic solvent is from about 5 parts to about 100 parts by weight based on the weight of the $\Delta^9$-THC; and in another embodiment, the amount of water-immiscible organic solvent is from about 5 parts to about 20 parts by weight based on the weight of the $\Delta^9$-THC.

The Caustic Contacting Step can be carried out by methods known in the art such as, but not limited to, stirring, shaking, countercurrent cascade, and ultrasound. admixing, pumping. The Caustic Contacting Step can also be carried out by methods useful for liquid-liquid extraction (see, e.g., Lo et al., Extraction, in 7 Kirk-Othmer *Encyc. of Chem. Technol.* 349-381 (4th ed. 1993), the entire contents of which are incorporated herein by reference).

The Caustic Contacting Step typically is carried out from about 0.25 hours to about 50 hours; in another embodiment, from about 0.25 hours to about 10 hours; and in another embodiment, from about 0.25 hours to about 2 hours.

The Caustic Contacting Step is typically carried at a temperature of from about 0° C. to about 100° C.; in another embodiment, from about 20° C. to about 50° C.; and in another embodiment, from about 20° C. to about 30° C.

The Caustic Contacting Step can be carried out at reduced pressure, atmospheric pressure (i.e., about 1 atmosphere), or elevated pressure. In one embodiment, the Caustic Contacting Step is carried out at atmospheric pressure.

The progress of the Caustic Contacting Step can be monitored using conventional techniques as described above for the Crystallizing Step.

In another embodiment, the trans-$\Delta^9$-THC Purification Method of the present invention further comprises contacting the alcoholic-caustic phase with an acid to provide an acid-treated alcoholic phase. Without being limited by theory, it is believed that trans-$\Delta^9$-THC is immiscible in the acidified alcoholic phase. Non-limiting examples of useful acids include citric acid, acetic acid, and the like. In one embodiment, the acid is citric acid.

Typically, the acid, is added in an amount sufficient to achieve a pH of from about 5 to about 9. In another embodiment, the acid is added in an amount sufficient to achieve a pH from about 6 to about 8; in another embodiment, the acid is added in an amount sufficient to achieve a pH of from about 7 to about 8.

In another embodiment, the $\Delta^9$-THC Purification Method of the present invention further comprises contacting the acid-treated alcoholic phase with a second water-immiscible organic solvent to form (i) a second organic phase comprising trans-(−)$\Delta^9$-THC and (ii) an acid-treated alcoholic phase.

Non-limiting examples of second water-immiscible organic solvents useful for contacting the acid-treated alcoholic phase to form a second organic phase comprising trans-$\Delta^9$-THC include the non-polar organic solvents described above for the Crystallizing Step. In one embodiment, the second water-immiscible organic solvent is heptane. The amount of first water-immiscible organic solvent used is typically is from about 1 part to about 1000 parts by weight based on the weight of the trans-$\Delta^9$-THC; in another embodiment, the amount of water-immiscible organic solvent is from about 1 part to about 50 parts by weight based on the weight of the trans-$\Delta^9$-THC; and in another embodiment, the amount of water-immiscible organic solvent is from about 1 part to about 10 parts by weight based on the weight of the trans-$\Delta^9$-THC. Methods useful for contacting the acid-treated alcoholic phase with a second water-immiscible organic solvent include those described above for the Caustic Contacting Step.

In another embodiment, the $\Delta^9$-THC Purification Method of the present invention further comprises separating the second organic phase from the acid-treated alcoholic phase. Methods useful for separating the second organic phase from the acid-treated alcoholic phase include those described above for separating the first organic phase from the alcoholic-caustic phase. After separation from the acid-treated alcoholic phase, the second organic phase is typically dried by, e.g., azeotropic distillation and/or contacting the second organic phase with a drying agent (e.g., $Na_2SO_4$ or $MgSO_4$).

In another embodiment, the $\Delta^9$-THC Purification Method of the present invention further comprises concentrating the second organic phase to form a concentrated second organic phase comprising trans-$\Delta^9$-THC. A non-limiting method useful for concentrating the second organic phase is distillation. When the second organic phase is concentrated by distillation, the distillation can be carried out at elevated pressure, atmospheric pressure, or at reduced pressure. In one embodiment, the distillation is carried out at atmospheric pressure. In another embodiment, the distillation is carried out at reduced pressure.

In another embodiment, the $\Delta^9$-THC Purification Method of the present invention further comprises contacting the concentrated second organic phase with a non-polar organic solvent to form a first organic composition comprising trans-$\Delta^9$-THC. The amount and type of non-polar organic solvent are those described above in the Crystallizing Step for the non-polar organic solvent.

In another embodiment, the trans-$\Delta^9$-THC used in the $\Delta^9$-THC Purification Method comprises trans-(−)-$\Delta^9$-THC. In another embodiment, the trans-$\Delta^9$-THC used in the $\Delta^9$-THC Purification Method comprises trans-(−)-$\Delta^9$-THC and trans-(+)-$\Delta^9$-THC. In another embodiment, the trans-$\Delta^9$-THC used in the $\Delta^9$-THC Purification Method comprises trans-(−)-$\Delta^9$-THC and trans-(+)-$\Delta^9$-THC, wherein the trans-(−)-$\Delta^9$-THC is present in an amount from about 0.75 to about 1.25 molar equivalents per molar equivalent of trans-(+)-$\Delta^9$-THC.

In another embodiment, the $\Delta^9$-THC Purification Method of the present invention further comprises:

adding trans-(−)-$\Delta^9$-THC or trans-(+)-$\Delta^9$-THC to the first organic composition in an amount sufficient to provide a second organic composition comprising (−)-$\Delta^9$-THC and trans-(+)-$\Delta^9$-THC, wherein the trans-(−)-$\Delta^9$-THC is present in an amount from about 0.75 to about 1.25 molar equivalents per molar equivalent of trans-(+)-$\Delta^9$-THC; and allowing trans-(−)-$\Delta^9$-THC and trans-(+)-$\Delta^9$-THC to crystallize from the first organic composition to provide crystalline (±)-$\Delta^9$-THC as described above for the Crystallizing Step.

In another embodiment, the $\Delta^9$-THC Purification Method of the present invention further comprises allowing the trans-(−)-$\Delta^9$-THC and trans-(+)-$\Delta^9$-THC to crystallize from the first organic composition to provide crystalline (±)-$\Delta^9$-THC as described above for the Crystallizing Step, wherein (a) the first organic composition comprises (−)-$\Delta^9$-THC and trans-(+)-$\Delta^9$-THC, and (b) the trans-(−)-$\Delta^9$-THC is present in first organic composition in an amount from about 0.75 to about 1.25 molar equivalents per molar equivalent of trans-(+)-$\Delta^9$-THC In another embodiment, the invention relates to a method for making crystalline (±)-$\Delta^9$-THC comprising:

allowing trans-(−)-$\Delta^9$-THC and trans-(+)-$\Delta^9$-THC to crystallize from a first composition comprising trans-(−)-$\Delta^9$-THC, trans-(+)-$\Delta^9$-THC, and a non-polar organic solvent to provide crystalline (±)-$\Delta^9$-THC, wherein the trans-(−)-$\Delta^9$-THC and the trans-(+)-$\Delta^9$-THC were obtained by:

(a) forming a biphasic composition comprising (i) a first organic phase comprising a first water-immiscible organic solvent, and (ii) an alcoholic-caustic phase containing trans-(−)-$\Delta^9$-THC and trans-(+)-$\Delta^9$-THC;

(b) separating the trans-(−)-$\Delta^9$-THC and the trans-(+)-$\Delta^9$-THC from the alcoholic-caustic phase; and (c) forming the first composition comprising (i) the trans-(−)-$\Delta^9$-THC and the trans-(+)-$\Delta^9$-THC of step (b), and (ii) the non-polar organic solvent.

Methods for forming the biphasic composition as well as the amounts and type of first water-immiscible organic solvent, water-miscible alcohol, water, and alkali metal hydroxide include those described above for the Caustic Contacting Step. Similarly, methods for separating the trans-(−)-$\Delta^9$-THC and the trans-(+)-$\Delta^9$-THC from the alcoholic-caustic phase, and methods for forming the first composition comprising (i) the trans-(−)-$\Delta^9$-THC and the trans-(+)-$\Delta^9$-THC of step (b), and (ii) the non-polar organic solvent include those described above for the (±)-$\Delta^9$-THC Purification Method.

Once obtained, crystalline (±)-$\Delta^9$-THC formed in the Crystallizing Step can be separated from the liquid phase by methods known in the art. Methods for separating the crystalline (±)-$\Delta^9$-THC from the liquid phase include, e.g., filtration, centrifugation and decantation. In one embodiment, crystalline (±)-$\Delta^9$-THC is separated from the liquid phase by filtration.

Crystalline (±)-$\Delta^9$-THC formed in the Crystallizing Step can, optionally, be washed with an organic wash solvent, and separated from the liquid phase as described above. When crystalline (±)-$\Delta^9$-THC is washed, the temperature of the organic wash solvent can vary. Typically, the washing, when done, is carried out with an organic wash solvent at a temperature from about −78° C. to about 50° C.; in another embodiment, from about −30° C. to about 30° C.; and in another embodiment, from about −20° C. to about 25° C.

Examples of useful organic wash solvents include the non-polar organic solvents described above. In one embodiment, the organic wash solvent, when used, is n-heptane.

The separated (±)-$\Delta^9$-THC can, optionally, be dried. The drying can be carried out at atmospheric pressure, optionally with the aid of a sweep gas such as dry air, nitrogen, helium, argon, or the like. Alternatively, the (±)-$\Delta^9$-THC can be dried at reduced pressure.

When the separated (±)-$\Delta^9$-THC is dried, the drying temperature can vary. Typically, the drying, when done, can be carried out at a temperature from about −25° to about 65° C.; in another embodiment, from about 0° to about 60° C.; and in another embodiment, from about 25° to about 50° C.

Typically, the (±)-$\Delta^9$-THC obtained in the Crystallizing Step comprises at least about 95% by weight of trans-(−)-$\Delta^9$-THC and trans-(+)-$\Delta^9$-THC based on the total amount of cannabinoids. In another embodiment, the (±)-$\Delta^9$-THC obtained in the Crystallizing Step comprises at least about 98% by weight of trans-(−)-$\Delta^9$-THC and trans-(+)-$\Delta^9$-THC based on the total amount of cannabinoids. In another embodiment, the (±)-$\Delta^9$-THC obtained in the Crystallizing Step comprises at least about 99% by weight of trans-(−)-$\Delta^9$-THC and trans-(+)-$\Delta^9$-THC based on the total amount of cannabinoids.

The separated (±)-$\Delta^9$-THC can then be resolved on a chiral stationary phase as described below in Section 4.4.

4.4. The Resolving Step

In the present invention, (±)-$\Delta^9$-THC obtained from crystalline (±)-$\Delta^9$-THC and an eluting solvent are contacted with a chiral stationary phase to resolve the trans-(−)- and (+)-enantiomers (the "Resolving Step"). This provides a composition comprising at least about 98% by weight of trans-(−)-$\Delta^9$-THC or trans-(+)-$\Delta^9$-THC based on the total amount of cannabinoids. Without being limited by theory, Applicants believe that resolving (±)-$\Delta^9$-THC obtained from crystalline (±)-$\Delta^9$-THC provides a trans-(−)-$\Delta^9$-THC or trans-(+)-$\Delta^9$-THC composition having low levels, if any, of the cannabinoid impurities found in trans-(−)-$\Delta^9$-THC or trans-(+)-$\Delta^9$-THC obtained by known methods.

The composition comprising (±)-$\Delta^9$-THC used in the Resolving Step can contain an amount of trans-(−)-$\Delta^9$-THC that is less than, equal to or greater than the amount of trans-(+)-$\Delta^9$-THC. For example, the composition comprising (±)-$\Delta^9$-THC may be obtained by admixing crystalline (±)-$\Delta^9$-THC with a trans-(−)-$\Delta^9$-THC composition and/or a trans-(+)-$\Delta^9$-THC prior to carrying out the Resolving Step. Typically, the composition comprising (±)-$\Delta^9$-THC contains about an equimolar amount of the trans-(−)-$\Delta^9$-THC and trans-(±)-$\Delta^9$-THC.

Any known or later-developed chiral stationary phase that resolves trans-(−)-$\Delta^9$-THC and trans-(+)-$\Delta^9$-THC can be used. For example, a method for resolving trans-(−)-$\Delta^9$-THC and trans-(+)-$\Delta^9$-THC enantiomers on a chiral stationary phase is described in S. L. Levin et al., *J. Chromatogr. A* 654:53-64 (1993)). Typically, the chiral stationary phase contains a chiral group or derivative immobilized on a support such as, e.g., a polymer or inorganic oxide. A non-limiting example of a useful polymer support is polystyrene in bead form. Non-limiting examples of useful inorganic oxide supports include silica, magnesium silicate, magnesia, alumina and molecular sieves. In one embodiment, the inorganic oxide support is silica.

The chiral derivative comprises at least one chiral center. Non-limiting examples of useful chiral derivatives include tris(arylcarbamate) derivatives of saccharides such as, e.g., amylose, cellulose, chitosin, xylan, curdlan, dextran, and inulan. In one embodiment, the saccharide is amylose.

In one embodiment, the tris(arylcarbamate) is tris(3,5-dimethylphenylcarbamate), tris(4-chlorophenylcarbamate), tris(4-methylcarbamate), tris(4-methylbenzoate) or tris[(S)-phenylethylcarbamate]. In another embodiment, the tris (arylcarbamate) is tris(3,5-dimethylphenylcarbamate). In another embodiment, the chiral stationary phase is amylose tris(3,5-dimethylcarbonate) immobilized on silica, available as Chiralpak® AD™ from Daicel Chemical Industries, Tokyo, Japan.

Other non-limiting examples of useful chiral stationary phases include cellulose triacetate; cellulose tribenzoate; poly[(S)—N-acrylolyphenylalanine ethyl ester]; 3,5-dinitrobenzoylphenylglycine; crosslinked di-(3,5-dimethylbenzoyl)-L diallyltartramide; crosslinked di-(4-tert-butylbenzoyl)-L diallyltartramide; and tetrahydro-aminophenanthrene 3,5-dinitrobenzamide (see E. R. Francotte, *J. Chromatogr. A* 906:379-397 (2001)).

Typically, a concentrated solution of $(\pm)$-$\Delta^9$-THC and an eluting solvent is added to the top (or front) of a column containing a chiral stationary phase. The $(\pm)$-$\Delta^9$-THC is then eluted with the eluting solvent (i.e., the mobile phase) to provide eluents containing trans-$(-)$-$\Delta^9$-THC or trans-$(+)$-$\Delta^9$-THC.

The Resolving Step can be carried using batch chromatography, continuous chromatography or simulated moving bed chromatography (see, e.g., E. R. Francotte, *J. Chromatogr. A* 906:379-397 (2001)). In one embodiment, the Resolving Step is carried using continuous chromatography.

The Resolving Step can be carried out at about 1 atmosphere of pressure or, optionally, at reduced pressure or elevated pressure. In one embodiment, the Resolving Step is carried out at about 1 atmosphere of pressure. In another embodiment, the Resolving Step is carried out at elevated pressure. In one embodiment, the Resolving Step is carried out at using flash chromatography at moderately elevated pressure, e.g., from about 1.1 to about 10 atmospheres; from about 1.1 to about 5 atmospheres; or from about 1.1 to about 1.3 atmospheres. In another embodiment, the Resolving Step is carried out at using flash chromatography at highly elevated pressure, e.g., from about 10 to about 175 atmospheres; from about 100 to about 175 atmospheres; from about 125 to about 175 atmospheres; or at about 150 atmospheres.

Non-limiting examples of eluting solvents useful in the Resolving Step include straight-chain or branch-chain $(C_1$-$C_4)$alkyls substituted with one or more —OH, —OR$_1$, —OC(O)R$_1$, —C(O)OR$_1$, -halo, or —CN; straight-chain or branch-chain $(C_4$-$C_{10})$aliphatic hydrocarbons; $(C_5$-$C_7)$cycloaliphatic hydrocarbon optionally substituted with one or more —R$_1$; $(C_4$-$C_7)$cyclic ethers optionally substituted with one or more —R$_1$; aromatic hydrocarbons optionally substituted with one or more —R$_1$, -halo, —CH$_2$(halo), —CH(halo)$_2$, —C(halo)$_3$ —O(C$_1$-C$_6$)alkyl; or any mixture thereof, where R$_1$ is $(C_1$-$C_4)$alkyl.

Non-limiting examples of straight-chain or branch-chain $(C_1$-$C_4)$alkyls substituted with one or more —OH, —OR$_1$, —OC(O)R$_1$, —C(O)OR$_1$, -halo, or —CN include methanol, ethanol, n-propanol, isopropanol, n-butanol, isobutanol, tert-butanol, chloromethane, methylene chloride, chloroform, carbon tetrachloride chloride, diethyl ether, di-isopropyl ether, tert-butyl methyl ether, acetonitrile, methyl formate, ethyl formate, methyl acetate, ethyl acetate, isopropyl acetate, butyl acetate, or any mixture thereof.

Non-limiting examples of straight-chain or branch-chain $(C_4$-$C_{10})$aliphatic hydrocarbons include butane, pentane, hexane, heptane, isooctane, nonane, decane, or any mixture thereof.

Non-limiting examples of $(C_5$-$C_7)$cycloaliphatic hydrocarbons optionally substituted with one or more —R$_1$ include cyclopentane, cyclohexane, methylcyclohexane, cycloheptane or any mixture thereof.

Non-limiting examples of $(C_4$-$C_7)$cyclic ethers optionally substituted with one or more —R$_1$ include tetrahydrofuran, methyltetrahydrofuran, 1,4-dioxane, 1,3-dioxolane, or any mixture thereof.

Non-limiting examples of aromatic hydrocarbons optionally substituted with one or more —R$_1$, -halo, —CH$_2$(halo), —CH(halo)$_2$, —C(halo)$_3$-O(C$_1$-C$_6$)alkyl include toluene, xylene, chlorobenzene, benzotrifluoride, or any mixture thereof.

In one embodiment, the eluting solvent comprises an aliphatic hydrocarbon and an alcohol. In another embodiment, the eluting solvent comprises n-heptane and iso-propanol. In another embodiment, the organic solvent comprises a (95:5 (v/v)) mixture of n-heptane:2-propanol.

The progress of the Resolving Step can be monitored using analytical methods described above in Section 4.3.

The eluents containing trans-$(-)$-$\Delta^9$-THC and being substantially free of other cannabinoids can be combined. In one embodiment, the eluents comprise at least about 98% by weight of trans-$(-)$-$\Delta^9$-THC; in another embodiment, at least about 99% by weight of trans-$(-)$-$\Delta^9$-THC; in another embodiment, at least about 99.5% by weight of trans-$(-)$-$\Delta^9$-THC; and in another embodiment, at least about 99.9% by weight of trans-$(-)$-$\Delta^9$-THC based on the total amount of trans-$(-)$-$\Delta^9$-THC and trans-$(+)$-$\Delta^9$-THC.

Similarly, eluents containing trans-$(+)$-$\Delta^9$-THC and being substantially free of other cannabinoids can be combined. In one embodiment, the eluents comprise at least about 98% by weight of trans-$(+)$-$\Delta^9$-THC; in another embodiment, at least about 99% by weight of trans-$(+)$-$\Delta^9$-THC; in another embodiment, at least about 99.5% by weight of trans-$(+)$-$\Delta^9$-THC; and in another embodiment, at least about 99.9% by weight of trans-$(+)$-$\Delta^9$-THC based on the total amount of trans-$(+)$-$\Delta^9$-THC and trans-$(-)$-$\Delta^9$-THC.

The eluents comprising a first solvent and trans-$(-)$-$\Delta^9$-THC or trans-$(+)$-$\Delta^9$-THC can, optionally, be separated from the volatiles to provide each enantiomer as an oil. Methods for separating the trans-$(-)$-$\Delta^9$-THC or trans-$(+)$-$\Delta^9$-THC from volatile components include, e.g., distillation at atmospheric pressure or reduced pressure. For example, the trans-$(-)$-$\Delta^9$-THC or trans-$(+)$-$\Delta^9$-THC can, if desired, be distilled by fractional distillation to provide a trans-$(-)$-$\Delta^9$-THC or trans-$(+)$-$\Delta^9$-THC distillate (see U.S. Pat. No. 4,381,399 to Olsen et al.).

4.5. Compositions Comprising trans-(−)-$\Delta^9$-THC or trans-(+)-$\Delta^9$-THC As noted above, the present invention also relates to compositions comprising trans-(−)-$\Delta^9$-THC or trans-(+)-$\Delta^9$-THC.

In one embodiment, the invention relates to a composition comprising at least 99.0% by weight of trans-(−)-$\Delta^9$-THC; in another embodiment, at least about 99.5% by weight of trans-(−)-$\Delta^9$-THC; and in another embodiment, at least 99.9% by weight of
trans-(−)-$\Delta^9$-THC based on the total amount of cannabinoids.

In one embodiment, the invention relates to a composition comprising at least 99.0% up to about 99.95% by weight of trans-(−)-$\Delta^9$-THC based on the total amount of cannabinoids. In another embodiment, the invention relates to a composition comprising at least 99.0% up to about 99.98% by weight of trans-(−)-$\Delta^9$-THC based on the total amount of cannabinoids.

In another embodiment, the compositions comprising at least 99.0% by weight of trans-(−)-$\Delta^9$-THC based on the total amount of cannabinoids are formulated as a pharmaceutical composition as described in Section 4.6.

In one embodiment, the invention relates to a composition comprising at least 99.0% by weight of trans-(+)-$\Delta^9$-THC; in another embodiment, at least 99.0.0% by weight of trans-(+)-$\Delta^9$-THC; in another embodiment, at least 99.5.0% by weight of
trans-(+)-$\Delta^9$-THC; and in another embodiment, at least 99.9% by weight of trans-(+)-$\Delta^9$-THC based on the total amount of cannabinoids.

The trans-(−)-$\Delta^9$-THC compositions of the present invention typically contain no $\Delta^9$-THC carboxylic acid, which can be found in trans-(−)-$\Delta^9$-THC compositions derived from natural sources (see R. F. Turk et al., *J. Pharm. Pharmac.* 23:190-195 (1971)). In one embodiment, the trans-(−)-$\Delta^9$-THC compositions of the present invention contain less than 0.05% $\Delta^9$-THC carboxylic acid; in another embodiment, less than 0.01% $\Delta^9$-THC carboxylic acid; in another embodiment, less than 0.005% $\Delta^9$-THC carboxylic acid; and in another embodiment, less than 0.001% $\Delta^9$-THC carboxylic acid based on the based on the total amount of cannabinoids. In another embodiment, the trans-(−)-$\Delta^9$-THC compositions contain no $\Delta^9$-THC carboxylic acid.

In another embodiment, the invention relates to a composition comprising at least 99.0% by weight of trans-(−)-$\Delta^9$-THC and less then of 0.05% of $\Delta^9$-THC carboxylic acid; in another embodiment, at least about 99.5% by weight of trans-(−)-$\Delta^9$-THC and less then 0.05% of $\Delta^9$-THC carboxylic acid; and in another embodiment, at least 99.9% by weight of trans-(−)-$\Delta^9$-THC and less then 0.05% of $\Delta^9$-THC carboxylic acid based on the total amount of cannabinoids.

In another embodiment, the invention relates to a composition comprising at least 99.0% by weight of trans-(+)-$\Delta^9$-THC and less then of 0.05% of $\Delta^9$-THC carboxylic acid; in another embodiment, at least about 99.5% by weight of trans-(+)-$\Delta^9$-THC and less then 0.05% of $\Delta^9$-THC carboxylic acid; and in another embodiment, at least 99.9% by weight of trans-(+)-$\Delta^9$-THC and less then 0.05% of $\Delta^9$-THC carboxylic acid based on the total amount of cannabinoids.

As noted above, trans-(+)-$\Delta^9$-THC, together with trans-(−)-$\Delta^9$-THC, is useful for making crystalline (±)-$\Delta^9$-THC.

The trans-(−)-$\Delta^9$-THC or trans-(+)-$\Delta^9$-THC compositions can be made by methods described above.

In another embodiment, the invention relates to a composition comprising (−)-$\Delta^9$-THC, trans-(+)-$\Delta^9$-THC, a first water-immiscible organic solvent, a water-miscible alcohol, water, and an alkali metal hydroxide. The composition is useful for removing impurities from (−)-$\Delta^9$-THC and/or trans-(+)-$\Delta^9$-THC.

4.6. Therapeutic/Prophylactic Administration of Compositions Comprising trans-(−)-$\Delta^9$-THC The compositions of the invention comprising at least 99.0% by weight of trans-(−)-$\Delta^9$-THC based on the total amount of cannabinoids are useful for treating the same diseases, ailments, or disorders ("Conditions") for which trans-(−)-$\Delta^9$-THC is known to be useful, or for any Condition for which trans-(−)-$\Delta^9$-THC is later found to be useful for treating or preventing. For example, trans-(−)-$\Delta^9$-THC compositions comprising at least 99.0% by weight of trans-(−)-$\Delta^9$-THC based on the total amount of cannabinoids can be used for treating nor preventing emesis, loss of weight loss of appetite, multiple sclerosis, Tourette's syndrome, Parkinson's disease, or palsies such as cerebral palsy. Accordingly, in one embodiment, the present invention also relates to methods for treating or preventing a Condition, comprising administering to a patient in need thereof an effective amount of a trans-(−)-$\Delta^9$ composition, wherein the trans-(−)-$\Delta^9$-THC composition comprises at least 99.0% by weight of trans-(−)-$\Delta^9$-THC; in another embodiment at least 99.0% by weight of trans-(−)-$\Delta^9$-THC; in another embodiment at least 99.5% by weight of trans-(−)-$\Delta^9$-THC; and in another embodiment at least 99.9% by weight of trans-(−)-$\Delta^9$-THC based on the total amount of cannabinoids.

In another embodiment, the present invention also relates to methods for treating or preventing a Condition, comprising administering to a patient in need thereof an effective amount of a trans-(−)-$\Delta^9$ composition, wherein the trans-(−)-$\Delta^9$-THC composition comprises at least 99.0% by weight of trans-(−)-$\Delta^9$-THC and less then 0.05% of $\Delta^9$-THC carboxylic acid; in another embodiment at least 99.0% by weight of trans-(−)-$\Delta^9$-THC and less then 0.05% of $\Delta^9$-THC carboxylic acid; in another embodiment at least 99.5% by weight of trans-(−)-$\Delta^9$-THC and less then 0.05% of $\Delta^9$-THC carboxylic acid; and in another embodiment at least 99.9% by weight of trans-(−)-$\Delta^9$-THC based on the total amount of cannabinoids and less then 0.05% of $\Delta^9$-THC carboxylic acid.

In one embodiment, the Condition is pain.

In another embodiment, the Condition is emesis, e.g., as the result of cancer chemotherapy.

In another embodiment, the Condition is loss of appetite.

In another embodiment, the Condition is weight loss, e.g., as the result of symptomative HIV infection including acquired immunodeficiency syndrome (AIDS) or AIDS related complex (ARC).

When administered to a patient, the trans-(−)-$\Delta^9$-TIC compositions containing at least about 99.0% by weight of trans-(−)-$\Delta^9$-THC based on the total amount of cannabinoids comprise a suitable amount of a pharmaceutically acceptable carrier so as to provide the form for proper administration to the patient.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the trans-(−)-$\Delta^9$-THC, containing at least about 99.0% by weight of
trans-(−)-$\Delta^9$-THC based on the total amount of cannabinoids, is administered. Such pharmaceutical carriers can be liquids, such as water and oils, including those of petroleum, animal, vegetable or synthetic origin, such as peanut oil, soybean oil, mineral oil, sesame oil, and the like. The pharmaceutical carriers can be saline, gum acacia, gelatin, starch paste, talc, keratin, colloidal silica, urea, and the like. In addition, auxiliary, stabilizing, thickening, lubricating and coloring agents may be used. The present compositions, if desired, can also contain minor amounts of wetting or emulsifying agents, and/or pH buffering agents. When administered to a patient, the pharmaceutically acceptable carriers are preferably sterile.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use.

In one embodiment, the trans-(−)-$\Delta^9$-THC composition containing at least about 99.0% by weight of trans-(−)-$\Delta^9$-THC based on the total amount of cannabinoids further comprises sesame oil. In another embodiment, the trans-(−)-$\Delta^9$-THC compositions containing at least about 99.0% by weight of trans-(−)-$\Delta^9$-THC based on the total amount of cannabinoids further comprises sesame oil, and the resultant admixture is encapsulated (see, e.g., U.S. Pat. No. 6,703,418 B2).

In another embodiment, the trans-(−)-$\Delta^9$-THC composition containing at least about 99.0% by weight of trans-(−)-$\Delta^9$-THC based on the total amount of cannabinoids is formed as a tablet.

The trans-(−)-$\Delta^9$-THC compositions containing at least about 99.0% by weight of trans-(−)-$\Delta^9$-THC based on the total weight of cannabinoids can be administered by any convenient route, for example by infusion or bolus injection, by absorption through epithelial or mucocutaneous linings (e.g., oral mucosa, rectal and intestinal mucosa, etc.) and may be administered together with another biologically active agent. Administration can be systemic or local. Various delivery systems are known, e.g., encapsulation in liposomes, microparticles, microcapsules, capsules, etc., and can be used to administer the pharmaceutical compositions. Methods of administration include but are not limited to intradermal, intramuscular, intraperitoneal, intravenous, subcutaneous, intranasal, epidural, oral, sublingual, intranasal, intracerebral, intravaginal, transdermal, rectally, by inhalation, or topically to the ears, nose, eyes, or skin. The preferred mode of administration is oral, but other modes of administration can be left to the discretion of the practitioner.

When used for oral delivery, the trans-(−)-$\Delta^9$-THC composition containing at least about 99.0% by weight of trans-(−)-$\Delta^9$-THC based on the total amount of cannabinoids can be in the form of tablets, lozenges, aqueous or oily suspensions, granules, powders, emulsions, capsules, syrups, or elixirs, for example. Orally administered compositions can contain one or more optional agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered pharmaceutical compositions. In these later platforms, fluid from the environment surrounding the capsule is imbibed by the driving compound, which swells to displace the agent or agent composition through an aperture. These delivery platforms can provide an essentially zero-order delivery profile as opposed to the spiked profiles of immediate release formulations. A time delay material such as glycerol monostearate or glycerol stearate may also be used. Oral compositions can include standard carriers such as mannitol, lactose, starch, magnesium stearate, sodium saccharine, cellulose, magnesium carbonate, etc. Such carriers are preferably of pharmaceutical grade.

When used for intravenous delivery, the trans-(−)-$\Delta^9$-THC composition containing at least about 99.0% by weight of trans-(−)-$\Delta^9$-THC based on the total amount of cannabinoids is formulated in accordance with routine procedures for intravenous administration to human beings. Preferably, the pharmaceutical compositions for intravenous administration are solutions in sterile isotonic aqueous buffer, optionally with a solublizing agent. Compositions for intravenous administration may optionally include a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the pharmaceutical compositions are to be administered by infusion, they can be dispensed, for example, with an infusion bottle containing sterile pharmaceutical grade water or saline, optionally with a solublizing agent. Where the pharmaceutical compositions are administered by injection, an ampoule of sterile water for injection or saline can be provided so that the ingredients can be mixed prior to administration.

The amount of the trans-(−)-$\Delta^9$-THC composition containing at least about 99.0% by weight of trans-(−)-$\Delta^9$-THC based on the total amount of cannabinoids that is effective in the treatment or prevention of a Condition can be determined by standard clinical techniques. In addition, in vitro or in vivo assays can optionally be employed to help identify optimal dosage amounts. The precise dose to be employed will also depend on the route of administration, and the seriousness of the Condition and can be decided according to the judgment of a practitioner and/or each animal's circumstances. When trans-(−)-$\Delta^9$-THC compositions containing at least about 99.0% by weight of trans-(−)-$\Delta^9$-THC based on the total amount of cannabinoids are administered orally, the effective dosage amount is from about 0.005 mg/kg of body weight to about 0.4 mg/kg of body weight about every 4 hours, although it is typically about 0.1 mg/kg of body weight or less. In one embodiment, the effective dosage amount is from about 0.005 mg/kg of body weight to about 0.4 mg/kg of body weight; in another embodiment, the effective dosage amount is from about 0.01 mg/kg of body weight to about 0.1 mg/kg of body weight; and in another embodiment, the effective dosage amount is from about 0.01 mg/kg of body weight to about 0.075 mg/kg of body weight.

The oral dosage forms typically comprise an amount of trans-(−)-$\Delta^9$-THC from about 0.1 mg to about 20 mg; in another embodiment, from about 2.5 mg to about 10 mg; in another embodiment, about 2.5 mg; in another embodiment, about 5 mg; and in another embodiment, about 10 mg.

In one embodiment, an effective dosage amount is administered about every 24 hours until the Condition is abated. In another embodiment, an effective dosage amount is administered about every 12 hours until the Condition is abated. In another embodiment, an effective dosage amount is administered about every 8 hours until the Condition is abated. In another embodiment, an effective dosage amount is administered about every 6 hours until the Condition is abated. And in another embodiment, an effective dosage amount is administered about every 4 hours until the Condition is abated.

In certain embodiments, it may be desirable to introduce the pharmaceutical compositions into the central nervous system by any suitable route, including intraventricular and intrathecal injection. Intraventricular injection may be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, the pharmaceutical compositions can be formulated as a suppository, with traditional binders and carriers such as triglycerides.

In another embodiment, the trans-(−)-$\Delta^9$-THC composition containing at least about 99.0% by weight of trans-(−)-$\Delta^9$-THC based on the total amount of cannabinoids can be delivered in a vesicle, in particular a liposome (see Langer, Science 249:1527-1533 (1990); Treat et al., in Liposomes in the Therapy of Infectious Disease and Cancer,
Lopez-Berestein and Fidler (eds.), Liss, New York, pp. 353-365 (1989); Lopez-Berestein, ibid., pp. 317-327; see generally ibid.).

In yet another embodiment, the trans-(−)-$\Delta^9$-THC composition containing at least about 99.0% by weight of trans-(−)-$\Delta^9$-THC based on the total amount of cannabinoids can be delivered in a controlled-release system. In one embodiment, a pump can be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Langer and Peppas, J. Macromol. Sci. Rev. Macromol. Chem. C23:61 (1983); see also Levy et al., Science 228:190 (1985); During et al., Ann. Neurol. 25:351 (1989); Howard et al., J. Neurosurg. 71:105 (1989)). In another embodiment, a controlled-release system can be placed in proximity of the target of the pharmaceutical compositions, thus requiring only a fraction of the systemic dose (see, e.g., Goodson, in Medical Applications of Controlled Release, supra, vol. 2, pp. 115-138 (1984)). Other controlled-release systems discussed in the review by Langer (Science 249:1527-1533 (1990)) can be used.

The invention also provides pharmaceutical packs or kits comprising one or more containers filled with the trans-(−)-$\Delta^9$-THC composition containing at least about 99.0% by weight of trans-(−)-$\Delta^9$-THC based on the total amount of cannabinoids. Optionally associated with such container(s) can be a notice in the form prescribed by a governmental agency regulating the manufacture, use or sale of pharmaceuticals or biological products, which notice reflects approval by the agency of manufacture, use or sale for human administration.

The following examples are set forth to assist in understanding the invention and do not limit the invention described and claimed herein. Such variations of the invention, including the substitution of all equivalents now known or later developed, which would be within the purview of those skilled in the art, and changes in formulations or minor changes in experimental design, fall within the scope of the present invention.

5. EXAMPLES

Unless otherwise stated, all reactions were carried out under argon or nitrogen atmosphere.

Unless otherwise stated, the phrase "cold water," "cold hexane," or "cold heptane" means water, hexane, or heptane, respectively, at a temperature of from about 0° to about 5° C.

Reagents and Solvents:

Unless otherwise stated, all reagents and solvents were purchased from Aldrich Chemical Company and used without further purification.

High Performance Liquid chromatography:

High performance liquid chromatography (HPLC) was carried out under the following conditions, and the purity of the samples eluents was calculated from the resultant area percentages:

Standard HPLC was carried out using a 3 μm $C_{18}$-stationary phase column (150×4.6 mm); a mobile phase of the following composition: THF (71%), MeOH (24%) and water (5%) for 25 min, gradient to THF (71%), MeOH (5%) and water (24%) in 10 min, and THF (71%), MeOH (24%) and water (5%) for 10 min; a flow rate of 1 mL/min; and a UV detector at 228 nm.

Chiral HPLC method 1 was carried out using a 20 μm Chiralpak AD 250×4.6 mm column; a mobile phase of heptane:isopropanol (95:5 (v:v)); a flow rate of 1 mL/min; and a UV detector at 228 nm. The concentration of the sample was about 1 mg per 1 mL of heptane.

Chiral HPLC method 2 was carried out using a 5 μm Chiralpak AD-H 250×4.6 mm (Diacel) column; a mobile phase of hexane:ethanol (95:5 (v:v)) for CBD and hexane:isopropanol (90:10 (v:v)) for $\Delta^9$-THC; a flow rate of 1 mL/min; and a UV detector at 228 nm. The concentration of the sample was about 1 mg per 1 mL of hexane.

Gas Chromatography:

Gas chromatography (GC) was carried out under the following conditions, and the purity of the eluents was calculated from the resultant area percentages:

Standard GC was carried using a HP-5 capillary column (length—30 m,
ID—0.25 mm); a stationary phase of 5% diphenyl/95% dimethyl)polysiloxane (0.25 μm film); an injection temperature of 230° C.; a detector/temperature (FID) of 270° C.; and an oven temperature program using a hold at 100° C. for 3 min, increasing to 240° C. at 10° C. per minute, holding at 240° C. for 10 min, increasing to 270° C. per min, and holding at 270° C. for 10 min. The concentration of the GC sample was about 1 mg per 1 mL of EtOH.

Chiral GC was carried out in a manner similar to that described above for standard GC, except that an Alpha-DEX-120, 30 m×0.25 mm column was used; the injection temperature was 250° C.; and the oven temperature was 90° C. (isothermal).

Powder X-Ray Diffraction Patterns:

Powder x-ray diffraction analysis was carried out by known methods using a PANALYTICAL (Philips) X'Pert Pro MPD x-ray powder diffraction system (CuK$_\alpha$ radiation, PW3050/60 goniometer, PW3011/20 proportional detector). The Bragg-Brentano scheme was used for beam focusing.

Nuclear Magnetic Resonance Spectroscopy:

Nuclear magnetic resonance (NMR) spectra were recorded on a Bruker AM-200 ($^1$H at 200 MHz, $^{13}$C at 50 MHz) or a Bruker AM-400 ($^1$H at 400 MHz) instruments using CDCl$_3$ (unless otherwise stated) as a solvent. Chemical shifts are in δ (ppm) relative to internal TMS.

Melting Points:

Melting point determinations were carried out in open capillary tubes using a Buchi B-545 capillary melting point apparatus or with a Mettler-Toledo FP-81 Melting point accessory with FP-900 processor. The melting points are uncorrected.

5.1. Example 1

Synthesis of (−)-cis-p-Menth-2,8-dien-1-ol

Preparation of (−)-(1R,2R,S5)-2-phenylthio-8-p-menthen-1-ol

A mixture of (−)-limonene oxide (152.2 g, 1.00 mol (about 1:1 cis:trans diastereomeric mixture) (Aldrich Chemical), thiophenol (60.6 g, 0.55 mol) (Fluka Chemical, Buchs, Switzerland), potassium carbonate (82.9 g, 0.60 mol), N,N-dimethylformamide (18.9 g, 0.26 mol) and toluene (400 mL) was stirred at 117° C. for 19 hours under an Ar atmosphere. The mixture was cooled to 25° C. and water (300 mL) was added. The resultant organic phase was collected, and the water layer was extracted with toluene (3×200 mL). The combined organic phases were washed with water (1×400 mL) and a 15% solution of brine (1×410 mL). The organic phase was then dried over $Na_2SO_4$ (30 g), filtered, and the resultant filtrate concentrated under pressure at 65° C. The resultant brown oil (200.5 g) was fractionally distilled under reduced pressure to provide (−)-cis-limonene oxide (33.7 g) (28.10 to 32.1° C. @1.1 mbar) and (−)-(1R,2R,4S)-2-phenylthio-8-p-menthen-1-ol (147.4 g) (128.10 to 138.2° C. @1.2 mbar) having a purity (GC) of 90.2%. An analytical sample of (−)-(1R,2R,4S)-2-phenylthio-8-p-menthen-1-ol had mp of 50-51° C. (hexane) and a purity (GC) of 99.0%.

Optical rotation: $[\alpha]_D^{20}$−110° (c=1.55, $CHCl_3$).
$^1$H NMR agreed with the structure.

Preparation of (1R,2R,4S)-1-Hydroxy-8-p-menthen-2-phenylsulfoxide (−)-(1R,2R,4S)-2-phenylthio-8-p-menthen-1-ol (147 g; 0.56 mol) was dissolved in methyl alcohol (1.35 L) with stirring at 25° C. under an Ar atmosphere, and the resultant solution was cooled to −10° to −5° C. A solution of OXONE® (potassium peroxymonosulfate) (279.1 g, 0.448 mol) (Aldrich Chemical) in water (1.35 L) was added dropwise to the methyl alcohol solution over 2 hours at −10° to −5° C., and the resultant mixture was stirred for an additional 30 min at −10° to −5° C. The mixture was warmed to 20° to 25° C., water (2.1 L) was added, and the resultant biphasic mixture was extracted with dichloromethane (3×910 mL). The combined organic phases were dried over sodium sulfate and filtered, and the resultant filtrate was concentrated under reduced pressure at 60° C. to provide 150.9 g of a residue. The residue was then purified by chromatography on a silica gel column (eluent: n-heptane/ethyl acetate 9:1 then 8:2). The fractions containing mainly (1R,2R,4S)-1-hydroxy-8-p-menthen-2-phenyl sulfoxide were combined and concentrated under vacuum for 10 hours at 40° to 50° C. to provide (1R,2R,4S)-1-hydroxy-8-p-menthen-2-phenyl sulfoxide as a mixture of two diastereomers. Yield: 86.1 g; 55.2%. The product was stored in freezer.

(−)-cis-p-Mentha-2,8-dien-1-ol

A mixture of (1R,2R,4S)-1-hydroxy-8-p-menthen-2-phenylsulfoxide (86 g, 0.31 mol) and piperidine (71.0 g, 0.83 mol) in dimethylsulfoxide (910 mL) was heated to 163° C. under a flowing Ar atmosphere, and the resultant mixture was stirred at 163° C. for 3 hours. The mixture was cooled to 20° to 25° C., treated with water (800 ml), and extracted with diethyl ether (2×400 mL). The combined organic phases were washed with 1N HCl (160 mL), a 7% solution of sodium hydrogen carbonate (150 mL), brine (150 mL), and dried over sodium sulfate. The organic phase was then concentrated under reduced pressure. The resultant residue (93.3 g) was purified by silica gel column chromatography (eluent: n-heptane followed by n-heptane:ethyl acetate (1:9 (v:v)), the fractions containing mainly (−)-cis-p-mentha-2,8-dien-1-ol were combined and concentrated under reduced pressure at 40° to 50° C. over 10 hours to provide (−)-cis-p-mentha-2,8-dien-1-ol. Yield: 26.1 g; 55%. Analysis (GC) of the product indicated that it was 90.9% pure.

Optical rotation: $[\alpha]_D^{25}$−690 (neat).
$^1$H NMR agreed with the structure.

5.2. Example 2

Synthesis of (+)-cis-p-Menth-2,8-dien-1-ol (+)-p-mentha-2,8-dien-1-ol was prepared as described in Example 1, except that (+)-limonene oxide (1:1 cis/trans diastereomeric mixture) was used instead of (−)-limonene oxide. Analysis (GC) of the resultant product indicated that it had a purity of 91.0%.

Optical rotation: $[\alpha]_D^{25}$+780 (neat).

5.3. Example 3

Synthesis of (±)-cis-p-Menth-2,8-dien-1-ol (±)-p-Mentha-2,8-dien-1-ol was prepared by mixing equivalent quantities of (−)-p-mentha-2,8-dien-1-ol of Example 2 with (+)-p-mentha-2,8-dien-1-ol of Example 1.

5.4. Example 4

Synthesis of (+)-CBD

Synthesis of crude (+)-CBD (3b)

A mixture of olivetol (3.6 g, 20 mmol), zinc chloride (3.5 g, 26 mmol), water (3.5 mL, 19 mmol) and dichloromethane (35 mL) was refluxed for 1 hour. A solution of (−)-p-mentha-2,8-dien-1-ol (3.0 g, 20 mmol) in dichloromethane (10 mL) was added drop-wise over 0.75 hour to the refluxing mixture, and the resultant reaction mixture was mixed for 0.5 hours at reflux. The mixture was cooled to 25° C., ice water (50 mL) was added, and the resultant biphasic mixture stirred for 20 minutes at 0° C. The resultant organic phase was collected, washed with water (2×20 mL) and 5% $NaHCO_3$ (20 mL). The organic phase was dried over $Na_2SO_4$, filtered, and concentrated under reduced pressure to provide 6.0 g of first crude (+)-CBD residue. Analysis (GC) of the first crude (+)-CBD residue indicated that it contained (+)-CBD (46.9%) and abn-(−)-CBD (19.7%). The first crude (+)-CBD residue was purified by column chromatography on silica gel (eluent MTBE/hexane) to provide 2.4 g of a second crude (+)-CBD residue.

Synthesis of (+)-CBD-bis(3,5-dinitrobenzoate) (4b)

A solution of 3,5-dinitrobenzoyl chloride (3.4 g, 14.7 mmol) in dichloromethane (10 mL) was added dropwise to a stirred mixture of the second crude (+)-CBD residue (2.4 g), 4, N,N-dimethylaminopyridine (0.05 g), pyridine (6 mL) and dichloromethane (15 mL) at 0° to 5° C. The mixture was allowed to warm to 25° C. and stirred for 2 hour at 25° C. The mixture was then poured into a mixture of 37% HCl (6 mL), ice (75 g) and dichloromethane (50 mL). The resultant organic phase was collected, washed with brine (15 mL), 5% NaHCO$_3$ (15 mL), dried over Na$_2$SO4, and filtered. The resultant filtrate was concentrated under reduced pressure to provide 5.2 g of crude (+)-CBD-bis(3,5-dinitrobenzoate) (4b). A solution of the crude (+)-CBD-bis(3,5-dinitrobenzoate) (5.2 g) in a 10:1 (vol:vol) mixture of isopropanol and ethylacetate (70 mL) was stirred overnight at 25° C. and filtered. The resultant precipitate was washed with 10:1 (vol:vol) mixture of isopropanol and ethylacetate (3×10 mL) and dried under reduced pressure to provide crystalline (+)-CBD-bis(3,5-dinitrobenzoate) (4b). Yield: 3.7 g, 26.5%.

Melting point: 90-92° C. (dec.).

Optical rotation: $[\alpha]_D^{20}$+80° (c=0.4, CHCl$_3$).

Synthesis of (+)-CBD (3b)

A mixture of the crystalline (+)-CBD bis(3,5-dinitrobenzoate) (4b) (3.5 g, 5.0 mmol), butylamine (3.7 g, 50 mmol) and toluene (20 mL) was stirred at room temperature for 12 hours and concentrated under reduced pressure. The resultant residue was purified by column chromatography on silica gel (eluent hexane:MTBE (70:1 (v:v)) to provide 1.3 g of (+)-CBD as an oil. A solution of the (+)-CBD (1.3 g) in hexane (1 mL) was kept overnight at −15° C. The resultant mixture was then filtered, and the resultant solids were dried under reduced pressure to provide
(+)-CBD (3b) as white crystals. Yield: 1.2 g, 64%. Analysis (GC) of the product indicated that it was 98.6% pure.

Melting point: 64-66° C.

Optical rotation: $[\alpha]_D^{20}$: +1260 (c=0.12, 95% EtOH).

5.5. Example 5

Preparation of (±)-Δ$^8$-THC

A solution of methanesulfonic acid (1.1 g, 11 mmol) in dichloromethane (6 mL) was added to solution of olivetol (10.0 g, 55.5 mmol) and (±)-p-mentha-2,8-dien-1-ol (8.5 g, 55.5 mmol) in dichloromethane (130 mL). The resultant mixture was refluxed for 4 hours with removal of water using a Dean-Stark separator. The mixture was then cooled to 25° C. and treated with aqueous NaHCO$_3$. The resultant organic phase was collected and concentrated under reduced pressure. The resultant residue was dissolved in heptane (110 mL) and washed with 10% NaOH (130 mL), and the resultant organic phases was concentrated under reduced pressure to provide 15.6 g of crude
(±)-Δ$^9$-THC. Analysis (GC) of the crude product indicated that it had a purity of 61.7%.

5.6. Example 6

Preparation of (−)-Δ$^8$-THC

Crude (−)-Δ$^8$-THC (2a) was prepared in a manner similar to that described in Example 5 for the preparation of crude (±)-Δ$^8$-THC, except that (+)-p-mentha-2,8-dien-1-ol was used instead of (±)-p-mentha-2,8-dien-1-ol.

5.7. Example 7

Preparation of (+)-Δ$^9$-THC

Crude (+)-Δ$^8$-THC (2b) was prepared in a manner similar to that described in Example 5 for the preparation of crude (±)-Δ$^8$-THC, except that (−)-p-mentha-2,8-dien-1-ol was used instead of (+)-p-mentha-2,8-dien-1-ol.

5.8. Example 8

Two-part Synthesis of trans-(−)-Δ$^9$-THC

Synthesis of (−)-CBD (3a)

A solution of (+)-p-mentha-2,8-dien-1-ol (84.5 g, 0.56 mol) in dichloromethane (325 mL) was added drop-wise over 1 hour to a stirred mixture of olivetol (100.0 g, 0.56 mol), zinc chloride (100.3 g, 0.72 mol), water (10.0 mL, 0.56 mol) and dichloromethane (1 L) at 40° C. The mixture was stirred for an additional 30 minutes at 40° C. The mixture was cooled to 25° C., poured into ice water (500 g), and the resultant biphasic mixture stirred for 20 minutes at 0° C. The resultant organic phase was collected and washed with cold water (2×250 mL). The organic phase was collected and concentrated under reduced pressure to provide a first residue (185.5 g). Analysis (GC) of the first residue indicated that it contained (−)-CBD (51.8%), abn-CBD (13.2%), olivetol (8.0%) and dialkylated olivetol (13.4%).

The first residue (185.5 g) was dissolved in n-heptane (1.1 L), and the resultant solution was admixed with a solution of 10% sodium hydroxide (1.3 L). The resultant organic phase was collected, washed with water (250 mL), and concentrated under reduced pressure to provide an oily-brown second residue (124.3 g). Analysis (GC) of the second residue indicated that it contained (−)-CBD (66.0%), abn-CBD (0.0%), olivetol (0.0%) and dialkylated olivetol (16.8%).

The second residue (124.3 g) was fractionally distilled (171°-178° C.; 0.1 mm Hg) to provide a 87.0 g of a distillate. Analysis (GC) of the distillated indicated that it contained 74.3% of (−)-CBD.

The distillate (87.0 g) was dissolved in heptane (425 mL) at 57° C. and filtered. The resultant filtrate was cooled to 0° to 5° C. and seeded with ~0.02 mg of powdered crystalline (−)-CBD (3a). The seeded solution was stirred at 0° to 5° C. for 5 hours then at −15° to −20° C. for 48 hours. The resultant mixture was filtered, and the resultant solids were washed with cold heptane. The solids were then dried under reduced pressure at 40° C. to provide (−)-CBD (3a). Yield: 39.2 g; 22%. Analysis (GC) of the product indicated that it contained (−)-CBD (3a) (97.1%) and trans-(−)-Δ$^9$-THC (1a) (1.44%). The structure of 3a was confirmed by $^1$H NMR spectroscopy. An analytical sample was prepared by recrystallizing a portion of the crude 3a from heptane as described above.

Melting point: 64°-65° C.

Optical rotation: $[\alpha]_D^{20}$−132° (c=0.12, 95% EtOH).

Synthesis of trans-(−)-Δ$^9$-THC (1a)

A solution of 15.0 g (47.8 mmol) of the crystallized (−)-CBD (3a) in anhydrous dichloromethane (45 mL) was added drop-wise over 1 hour to a stirred solution of BF$_3$.Et$_2$O (8.4 g, 59.2 mmol) in anhydrous dichloromethane (180 mL) at −10° C. under an Ar atmosphere. The mixture was stirred for 2 hours at −10° C. and poured into ice water (100 g). The resultant biphasic mixture was further stirred for 20 minutes at 0° C. The resultant organic phase was collected, washed with cold water (50 mL), 7% aqueous sodium bicarbonate (50 mL), and water (50 mL). The organic phase was dried with Na$_2$SO$_4$ and filtered. The resultant filtrate was concentrated under reduced pressure at 40° C. to provide trans-(−)-Δ$^9$-THC (1a) as a yellow oil. Yield: 14.9 g, 99%. Analysis (CG) of the product indicated that it contained 81.9% of trans-(−)-Δ$^9$-THC (1a).

5.9. Example 9

One-Pot Synthesis of trans-(−)-Δ$^9$-THC

A mixture of olivetol (50.0 g, 0.28 mol), zinc chloride (50.0 g, 0.36 mol) and anhydrous dichloromethane (510 mL) was stirred at 40° C. for 1 hour under an Ar atmosphere. A solution of (+)-p-mentha-2,8-dien-1-ol (42.2 g, 0.28 mol) and dichloromethane (155 mL) was added drop-wise over 1 hour to the stirred olivetol-containing mixture, and the resultant mixture was stirred for an additional 40 minutes at 40° C. The mixture was cooled to −10° C., and a solution of BF$_3$.Et$_2$O (23.6 g, 166 mmol) in anhydrous dichloromethane (37 mL) was added dropwise over one hour. The resultant mixture was stirred for 1.5 hours at −10° C. Cold water (250 mL) was added, and the resultant organic phase was collected and washed with cold water (120 mL), 7% aqueous sodium bicarbonate (120 mL), and water (120 mL). The organic phase was dried with Na$_2$SO$_4$ (30 g) and filtered. The resultant filtrate was concentrated under reduced pressure to provide trans-(−)-Δ$^9$-THC (1a) as a brown oil. Yield: 89.14 g, 46% based on the trans-(−)-Δ$^9$-THC content in the oil. Analysis (GC) of the product indicated that it contained trans-(−)-Δ$^9$-THC (1a) (45.1%), (−)-Δ$^8$-THC (5.06%) (2a), (−)-Δ$^8$-iso-THC (17.6%), CBD (3a) (0.71%), olivetol (7.95%) and dialkylated olivetol (10.8 wt. %); no trans-(+)-Δ$^9$-THC (1b) was detected.

A solution of the trans-(−)-Δ$^9$-THC oil (20.0 g) in heptane (120 mL) was thoroughly washed with 10% NaOH (150 mL) and water (50 mL), dried over Na$_2$SO$_4$, and filtered. The resultant filtrate was then concentrated under reduced pressure to provide a first crude residue (16.6 g) containing 38.5 wt. % of trans-(−)-Δ$^9$-THC (1a) using HPLC; and trans-(−)-Δ$^9$-THC (1a) (47.4%), Δ$^8$-THC (2a) (8.6%), Δ$^8$-iso-THC (19.6%), CBD (0.5%), olivetol (0.0%) and dialkylated olivetol (10.9%) using GC.

A solution of the first crude residue (16.5 g) in heptane (240 mL) was extracted with an aliquot of 9% NaOH in 80% methanol (3×180 mL). The combined basic methanolic extracts were acidified to approximately pH 7 with 20% citric acid and extracted with heptane (3×90 mL). The combined organic fractions were washed with water (50 mL), dried over Na$_2$SO$_4$, and filtered. The resultant filtrate was then concentrated under reduced pressure to provide 13.7 g of crude residue which contained 44.0 wt. % of trans-(−)-Δ$^9$-THC using HPLC; and trans-(−)-Δ$^9$-THC (1a) (51.8%), Δ$^8$-THC (2a) (10.0%), Δ$^8$-iso-THC (22.3%), CBD (0.0%), olivetol (0.0%) and dialkylated olivetol (1.3%) using GC.

5.10. Example 10

Synthesis of trans-(+)-Δ$^9$-THC

A solution of BF$_3$.Et$_2$O (0.34 g, 2.4 mmol) in anhydrous dichloromethane (8 mL) was added dropwise with stirring over 1 hour to a solution of the crystalline (+)-CBD (3a) from Example 4 (1.1 g, 3.6 mmol) in anhydrous dichloromethane (50 mL) at −5° C. The resultant mixture was stirred for 1.5 hours at −5° C. The mixture was added to a mixture of ice (100 g) and 7% NaHCO$_3$ (100 mL). The resultant organic phase was collected and the aqueous phase extracted with dichloromethane (2×20 mL). The combined organic phases were washed with water (20 mL), dried with Na$_2$SO$_4$, and filtered. The resultant filtrate was concentrated under reduced pressure at 40° C. The resultant residue was purified by column chromatography on silica gel (stationary phase) using MTBE:hexane (1:100 to 3:100 (v:v)) as eluent to provide crude trans-(+)-Δ$^9$-THC (1b) as a yellow oil: Yield: 0.7 g. Analysis (GC) of the crude trans-(+)-Δ$^9$-THC indicated that it had a purity of 92.6%.

5.11. Example 11

One-pot Synthesis of trans-(+)-Δ$^9$-THC

A mixture of olivetol (14.21 g, 79.6 mmol), zinc chloride (14.25 g, 102.6 mmol) and anhydrous dichloromethane (145 mL) was stirred at 40° C. for 1 hour. A solution of (−)-p-mentha-2,8-dien-1-ol (12.00 g, 76.6 mol) and anhydrous dichloromethane (45 mL) was added drop-wise over 1 hour at 40° C. to the stirred olivetol-containing mixture, and the resultant mixture was stirred for an additional 40 minutes at 40° C. The mixture was cooled to −10° C., and a solution of BF$_3$.Et$_2$O (6.7 g, 47 mmol) in anhydrous dichloromethane (12 mL) was added drop-wise over 1 hour at −10° C. The mixture was stirred for 30 minutes at −10° C. Cold water (50 mL) was added, and the resultant biphasic mixture was stirred for an additional 20 minutes at 0° C. The resultant organic phase was collected, washed with cold water (2×50 mL), 5% aqueous sodium bicarbonate (50 mL), and water (50 mL). The organic phase was then concentrated under reduced pressure at 40° C., and the resultant residue (24.8 g) was dissolved in n-heptane (140 mL) at 25° C. The resultant solution was washed with 10% aqueous KOH (124 mL), water (2×50 mL), dried with MgSO$_4$ (10 g), and filtered. The resultant filtrate was concentrated under reduced pressure at 40° C. The resultant residue (20.7 g) was then fractionally distilled at reduced pressure (0.1 mbar) to provide trans-(+)-Δ$^9$-THC (1b). Yield: 17.16 g, 69%. Analysis (GC) of the product indicated that it contained trans-(+)-Δ$^9$-THC (1b) (49.2%), Δ$^8$-iso-THC (25.31%) and dialkylolivetol (1.29%); no trans-(−)-Δ$^9$-THC (1a) was detected.

5.12. Example 12

Synthesis of (±)-Δ$^9$-THC

A solution of BF$_3$.Et$_2$O (0.3 g, 2.1 mmol) in anhydrous dichloromethane (8 mL) was added dropwise with stirring over 1 hour to a solution of (±)-CBD (1.0 g, 3.2 mmol) in anhydrous dichloromethane (45 mL) at −5° C. The resultant mixture was stirred for 1.5 hours at −5° C. The mixture was then added to 7% NaHCO$_3$ (50 mL). The resultant organic phase was collected and the aqueous phase extracted with dichloromethane (3×30 mL). The combined organic phases were washed with brine (20 mL), dried with Na$_2$SO$_4$ and filtered. The resultant filtrate was concentrated under reduced pressure. The resultant residue was purified by column chromatography on silica gel (stationary phase) and MTBE:hexane (1:100 to 2:100 (v:v)) as eluent to provide crude (±)-Δ$^9$-THC as a yellow oil. Yield: 0.6 g, 56%. Analysis (GC) of the (±)-Δ$^9$-THC oil indicated that it had a purity of 92.6% purity. The oily (±)-Δ$^9$-THC (0.6 g) was dissolved in hexane (0.5 mL), and the resultant mixture was maintained at −15° C. for 24 hours. The resultant mixture was filtered, washed with cold hexane (3×1 mL) and dried under reduced pressure to provide (±)-Δ$^9$-THC as slightly rose crystals. Yield: 0.4 g. Melting point: 65-66° C.

5.13. Example 13

One-Pot Synthesis of (±)-Δ⁹-THC

A mixture of olivetol (11.84 g, 65.7 mmol), zinc chloride (11.87 g, 85.4 mmol) and anhydrous dichloromethane (120 mL) was stirred at 40° C. for 1 hour. A solution of (+)-p-mentha-2,8-dien-1-ol (5.00 g, 32.84 mol), (−)-p-mentha-2,8-dien-1-ol from Example 1 (5.00 g, 32.84 mol) and anhydrous dichloromethane (37 mL) was added drop-wise over 1 hour at 400 to the stirred olivetol-containing mixture, and the resultant mixture was stirred for an additional 40 minutes at 40° C. The mixture was cooled to −10° C., and a solution of $BF_3.Et_2O$ (5.6 g, 39.4 mmol) in anhydrous dichloromethane (10 mL) was added drop-wise over 1 hour at −10° C. The mixture was stirred for 30 minutes at −10° C., and 50 mL of cold water were added. The resultant biphasic mixture was stirred for an additional 20 minutes at 0° C. The resultant organic phase was collected and washed with cold water (2×50 mL), 8% aqueous sodium bicarbonate (50 mL), and water (50 mL). The organic phase was concentrated under reduced pressure at 40° C. The resultant residue (20.5 g) was dissolved in n-heptane (115 mL) at 25° C. and washed with 10% aqueous KOH (100 mL) for 40 min at 25° C. and water (50 mL). The organic phase was then concentrated under reduced pressure at 50° C. to provide 17.1 g of crude (±)-Δ⁹-THC as a brown oil.

A portion of the crude (±)-Δ⁹-THC oil (2.4 g) was dissolved in a minimal amount of heptane and purified by chromatography in a single pass using a Merck-Knauer PP K-1800 preparative chromatograph with one cylinder (50 mm×210 mm of LUNA CM 10 μm; loading capacities 600 mg; eluent: n-heptane). Fractions containing (±)-Δ⁹-THC were combined and concentrated under reduced pressure at 40° C. to provide (±)-Δ⁹-THC (1). Yield: 1.1 g. Analysis (GC) of the product indicated that it contained (±)-Δ⁹-THC (1) (91.27%), iso-Δ⁹-THC (1.87%) and Δ⁸-THC (1.08%).

5.14. Example 14

Preparation of (+)-Δ⁹-THC

A mixture of olivetol (15.0 g, 83.2 mmol), zinc chloride (15.0 g, 108 mmol) and anhydrous dichloromethane (150 mL) was stirred at 40° C. for 1 hour. A solution of (±)-p-mentha-2,8-dien-1-ol (12.7 g, 83.2 mmol) and anhydrous dichloromethane (45 mL) was added drop-wise over 1 hour at 400 to the stirred olivetol-containing mixture, and the resultant mixture was stirred for an additional 0.50 hours at 40° C. The mixture was cooled to −10° C., and a solution of $BF_3.Et_2O$ (7.1 g, 49.4 mmol) in anhydrous dichloromethane (11 mL) was added drop-wise to the mixture over 1 hour at −10° C. The mixture was stirred for 0.50 hours at −10° C., and 80 mL of cold water was added with stirring to form a biphasic mixture. The organic phase was collected and washed with cold water (80 mL), 5% aqueous sodium bicarbonate (80 mL), and water (80 mL). The organic phase was dried over $Na_2SO4$ and filtered, and the resultant filtrate was concentrated under reduced pressure to provide 28.5 g of a first crude (±)-Δ⁹-THC residue. Analysis of the residue indicated that it contained (±)-Δ⁹-THC (30.3%) using HPLC; and (±)-Δ⁹-THC (45.2%), Δ⁸-THC (3.2%), (±)-Δ⁹-iso-THC (17.3%). CBD (4.0%), olivetol (8.3%), and dialkylated olivetol (11.7%) using GC.

A portion of the first crude (±)-Δ⁹-THC residue (28.5 g) was dissolved in heptane (165 mL), and the resultant solution was washed with 10% NaOH (200 mL) and water (80 mL). The organic solution was then dried by azeotropic distillation and concentrated under reduced pressure to provide a second crude (±)-Δ⁹-THC residue. Yield: 23.5 g, 37.6%. Analysis of the second crude (±)-Δ⁹-THC residue indicated that it contained (±)-Δ⁹-THC (37.6%) using HPLC; and (±)-Δ⁹-THC (50.7%), Δ⁸-THC (3.8%), (±)-Δ⁸-iso-THC (19.6%), CBD (4.4%), olivetol (0.0%), and dialkylated olivetol (12.8%) using GC.

5.15. Example 15

Preparation of (±)-Δ⁹-THC from a Mixture of Crude of trans-(−)-Δ⁹-THC and trans-(+)-Δ⁹-THC Trans-(−)-Δ⁹-THC was prepared as described in Example 14 for preparing the crude second (±)-Δ⁹-THC residue, except that (+)-p-mentha-2,8-dien-1-ol was used instead of (±)-p-mentha-2,8-dien-1-ol. Analysis (HPLC) of the resultant crude trans-(−)-Δ⁹-THC indicated that it contained 41.4% by weight of trans-(−)-Δ⁹-THC.

Trans-(+)-Δ⁹-THC was prepared as described in Example 14 for preparing the crude second (±)-Δ⁹-THC residue, except that (−)-p-mentha-2,8-dien-1-ol was used instead of (±)-p-mentha-2,8-dien-1-ol. Analysis (HPLC) of the resultant crude trans-(+)-Δ⁹-THC indicated that it contained 37.5% by weight of trans-(−)-Δ⁹-THC.

The crude trans-(−)-Δ⁹-THC (24.3 g; 10.0 g of trans-(−)-Δ⁹-THC) and trans-(+)-Δ⁹-THC (26.7 g; 10.0 g of trans-(+)-Δ⁹-THC) were dissolved in heptane (425 mL) at 25° C. The resultant solution was admixed with 2×180 mL of a solution of 9% aqueous NaOH:methanol (20:80 (v:v)). The methanolic phases were combined and treated with 10% citric acid at 0° C. to about 5° C. until the pH was about 7. Heptane (290 mL) was added, and the resultant organic phase was washed with water. The organic phase was then dried over $Na_2SO_4$ and filtered, and the resultant filtrate was concentrated under reduced pressure to provide 41.8 g of crude (±)-Δ⁹-THC as a brown oil. Analysis (HPLC) of the crude (±)-Δ⁹-THC indicated that it had a purity of 48%.

The crude (±)-Δ⁹-THC (41.8 g) was dissolved in heptane (85 mL), and the resultant solution was cooled to 0° C. and seeded with crystalline (±)-Δ⁹-THC (100 mg). The resultant mixture was further cooled to −15° C. for 12 hour and filtered. The resultant solids were washed with cold heptane (3×10 mL) and dried under reduced pressure to provide (±)-Δ⁹-THC as a white crystalline solid. Yield: 8.7 g, 43%. Analysis (HPLC) of the product indicated that it had a purity of 96.5%. The crystalline (±)-Δ⁹-THC remained white after at least three days at 25° C.

5.16. Example 16

Preparation of (t)-Δ⁹-THC from (t)-Δ⁸-THC

Preparation of (J)-9-chloro-trans-hexahydrocannabinol

A mixture of crude (±)-Δ⁸-THC from Example 5 (15.6 g; 9.63 g of (±)-Δ⁸-THC), zinc chloride (4.66 g, 34.23 mmol) and anhydrous dichloromethane (310 mL) was stirred for 0.5 hours at 25° C. under an Ar atmosphere. The mixture was cooled to 0° C., and gaseous hydrogen chloride was bubbled through the mixture for 1.5 hours. The mixture was poured into an ice bath (150 g), and the resultant biphasic mixture was stirred for 1 hour at 0 to 5° C. The organic phase was collected and washed with cold water (2×100 mL), 8% sodium bicarbonate solution (100 mL), and water (100 mL).

The organic phase was dried over anhydrous $Na_2SO_4$ (15 g), and filtered. The resultant filtrate was then concentrated under reduced pressure at 30° C. The resultant residue (16.3 g) was dissolved in n-heptane (33 mL), cooled to 0° C., and seeded with (±)-9-chloro-trans-hexahydrocannabinol (0.01 g). The resultant mixture was then stirred at 0° C. for 5 hours, cooled to −15° C., and stirred at −15° C. for 60 hours. The mixture was filtered and the resultant solids washed with cold n-heptane (14 mL). The solids were then dried under reduced pressure at 50° C. to provide (±)-9-chloro-trans-hexahydrocannabinol. Yield: 5.7 g; 32.7%. Analysis (HPLC) of the (±)-9-chloro-trans-hexahydrocannabinol indicated that it had a purity of 95.2%. An analytical sample, recrystallized from heptane, had a melting point of 89-90° C. The purity (HPLC) of the analytical same was 99.6%.

Optical rotation: $[\alpha]_D^{20}$ 0.0° (c=0.53, $CHCl_3$).

$^1$H NMR agreed with the structure.

$^{13}$C NMR ($CDCl_3$) δ 13.9, 19.1, 22.4, 24.2, 27.6, 30.4, 31.3, 31.5, 34.1, 35.3, 42.0, 44.8, 48.7, 72.6, 76.7, 107.7, 108.9, 110.0, 142.8, 154.5, 155.0.

The x-ray powder diffraction pattern of the crystalline (±)-9β-Cl—HHC had characteristic peaks expressed in degrees 2θ at approximately 7.5, 11.2, 13.3, 14.9, 15.4, 15.9, 19.4, 19.7, 20.0 and 22.5.

Preparation of (±)-Δ$^9$-THC

A mixture of potassium-tert-amylate (6.6 g), (±)-9-chloro-trans-hexahydrocannabinol (5.7 g, 16.2 mmol) and anhydrous toluene (280 mL) was stirred for 75 minutes at 65° C. The mixture was cooled to 25° C. and poured into ice water (100 g). The resultant organic phase was collected and washed with cold water (2×100 mL), 7% sodium bicarbonate, and water (2×100 mL). The organic phase was then dried over anhydrous $Na_2SO_4$ and concentrated under reduced pressure. The resultant residue (5.35 g) was dissolved in n-heptane (3.4 mL), cooled to 0° C., and seeded with (±)-Δ$^9$-THC (0.01 g). The resultant mixture was stirred at 0° C. for 5 hours, cooled to −15° C., and stirred at −15° C. for 60 hours. The mixture was filtered and the resultant solids washed with cold n-heptane (4 mL). The solids were then dried under reduced pressure at 50° C. to provide (±)-Δ$^9$-THC. Yield: 3.3 g, 64.7%. Analysis (HPLC) of the product indicated that it had a purity of 97.23%.

5.17. Example 17

Purification of (±)-Δ$^9$-THC

Preparation of (±)-Δ$^9$-THC m-nitrobenzenesulfonate

A mixture of the second crude (±)-Δ$^9$-THC residue of Example 14 (20.0 g; 7.52 g of (±)-Δ$^9$-THC), 3-nitrobenzenesulfonyl chloride (14.5 g, 65.4 mmol), triethylamine (9.7 g) and dichloromethane (300 mL) was stirred at 25° C. for 1 hour. The resultant admixture was then treated with cold water (200 mL). The resultant organic phase was collected and washed sequentially with 10% HCl (80 mL), water (100 mL), 5% $NaHCO_3$ (100 mL) and water (100 mL). The organic phase was then dried over $Na_2SO_4$ and filtered. The resultant filtrate was concentrated under reduced pressure to provide 25.8 g of a first crude (±)-Δ$^9$-THC m-nitrobenzenesulfonate residue. Analysis (HPLC) of the first crude (±)-Δ$^9$-THC m-nitrobenzenesulfonate residue indicated that it had a purity of 42.9 wt. %.

The first crude (±)-Δ$^9$-THC m-nitrobenzenesulfonate residue was dissolved in isopropanol (95 mL) at 50° C. The resultant solution was cooled to room temperature, seeded with powdered crystalline (±)-Δ$^9$-THC m-nitrobenzenesulfonate, cooled to 0° C., and stirred for 12 hour at 0° C. The resultant mixture was filtered, and the resultant solids were washed with cold heptane (65 mL). The solids were then dried under reduced pressure to provide 10.3 g of second crude (±)-Δ$^9$-THC m-nitrobenzenesulfonate residue as a yellow solid. Analysis (HPLC) of the second crude (±)-Δ$^9$-THC m-nitrobenzenesulfonate residue indicated that it had a purity of 79.1%.

The second crude (±)-Δ$^9$-THC m-nitrobenzenesulfonate (10.0 g) was dissolved in dichloromethane (13 mL), and the resultant solution was added to a distillation pot equipped with a 10 cm Vigreux column and an addition port. The contents of the distillation pot were then distilled while isopropanol (40 mL) was continuously added dropwise to the mixture through the addition port. The distillation was stopped when the temperature of vapors in the head of the column reached 82.4° C. The contents of the distillation pot where cooled to 0° C. to 5° C., and the resultant suspension was stirred for 12 hours at 0° C. to about 5° C. The suspension was filtered, and the resultant solids were washed with cold heptane (22 mL). The solids were then dried under reduced pressure to provide crystalline (±)-Δ$^9$-THC m-nitrobenzenesulfonate. Yield: 7.0 g, 59%. Analysis (HPLC) of the product indicated that it had a purity of 99.0%.

Melting point: 105-107° C.

X-ray powder diffraction pattern: Characteristic peaks expressed in degrees 2θ where observed at approximately 9.3, 10.6, 12.5, 15.2, 18.7, 19.3, 21.2 and 22.9.

Preparation of (±)-Δ$^9$-THC

A mixture of the crystalline (±)-Δ$^9$-THC m-nitrobenzenesulfonate (4.5 g, 7.5 mmol), 50% NaOH (5.3 g), and methanol (110 mL) was stirred at 50° C. for about 1-2 hours then cooled to room temperature. The cooled mixture was then treated with cold water (1×150 mL) followed by treatment with 10% HCl until the pH was about 7. The resultant mixture was extracted with heptane (3×75 mL), and the combined organic extracts were washed with 7% $NaHCO_3$ (100 mL) and water (100 mL). The organic phase was dried over $Na_2SO_4$ and filtered. The resultant filtrate was then concentrated under pressure to provide 2.5 g of crude (±)-Δ$^9$-THC. Analysis (HPLC) of the crude product indicated that it contained 92.6% by weight of (±)-Δ$^9$-THC.

The crude (±)-Δ$^9$-THC was dissolved in heptane (5 mL) at 40° C. The resultant solution was cooled to 0° C., seeded with powdered crystalline (±)-Δ$^9$-THC, and stirred for 12 hours at −15° C. The resultant mixture was filtered and the resultant solids washed with cold heptane (3.5 mL). The solids were then dried under reduced pressure to provide (±)-Δ$^9$-THC as off-white crystals. Yield: 2.1 g, 74%. The crystalline (±)-Δ$^9$-THC was stable at 25° C. in the presence of air and laboratory lighting. Analysis (HPLC) of the product indicated that it had a purity of 99.0%. An analytical sample that was recrystallized from hexane had a melting point of 65°-66° C.

Optical rotation: $[\alpha]_D^{20}$ 0.0° (c=0.53, $CHCl_3$).

$^1$H NMR: The spectra of the product agreed with the structure.

5.18. Example 18

Preparation of (±)-Δ$^9$-THC from trans-(−)-Δ$^9$-THC and trans-(+)-Δ$^9$-THC

A solution of trans-(−)-Δ$^9$-THC (1a) (10 g; 9.35 g of trans-(−)-Δ$^9$-THC based on a purity of 93.5%), trans-(+)-Δ$^9$-THC (1b) from Example 11 (17.0 g, 8.36 g based on a purity of 49.2%) and heptane (28 mL) was cooled to 0° C., seeded with (±)-$\Delta^9$-THC (0.02 g), and stirred for 5 hours at 0° C. The resultant mixture was cooled to −15° C. and stirred for an additional 48 hours at −15° C. The mixture was filtered and the resultant solids washed with cold n-heptane (4 mL). The solids were then dried under reduced pressure at 35° C. to provide crude (±)-$\Delta^9$-THC. Yield: 11.4 g, 68%. Analysis (HPLC) of the crude (±)-$\Delta^9$-THC indicated that it had a purity of 93.6%.

The crude (±)-$\Delta^9$-THC (11.2 g) was dissolved in heptane (15 g) at 50° C., and the mixture was cooled with stirring to 0° C. The resultant mixture was stirred at 0° C. for 2 hours, cooled to −15° C., and stirred for an additional 48 hours at −15° C. The mixture was filtered and the resultant crystalline solids washed with cold n-heptane (4 mL). The solids were then dried under reduced pressure at 35° C. to provide crystalline (±)-$\Delta^9$-THC. Yield: 9.2 g, 82%. Analysis (HPLC) of the crystalline (−)-$\Delta^9$-THC indicated that it had a purity of 97.7%.

5.19. Example 19

Preparation of Crystalline (±)-$\Delta^9$-THC (+)-$\Delta^9$-THC (2.70 g, 2.55 g of trans-(+)-$\Delta^9$-THC based on a purity of 94.3%) (obtained from enantioselective chromatography of crystalline (±)-$\Delta^9$-THC) as described in Example 21) and trans-(−)-$\Delta^9$-THC from Example 9 (3.36 g, 2.76 g of trans-(−)-$\Delta^9$-THC based on purity of 82.2%) were dissolved in heptane (9.5 mL). The resultant solution was cooled to 0° C. and seeded with crystalline (±)-$\Delta^9$-THC (0.01 g). The resultant admixture was stirred for 5 hours at 0° C. and for 72 hour at −15° C. The resultant mixture was filtered and the resultant solids washed with cold heptane (8 mL). The solids were then dried under reduced pressure at 35° C. to provide crystalline (±)-$\Delta^9$-THC. Yield: 4.4 g, 79.7%. Analysis (HPLC) of the product indicated that it had a purity of 98.7%.

5.20. Example 20

Preparation of Crystalline (±)-$\Delta^9$-THC

Crude trans (−)-$\Delta^9$-THC and crude trans-(+)-$\Delta^9$-THC were prepared by processes as described in Examples 9 and 11, respectively. Crude trans-(−)-$\Delta^9$-THC (27.7 g; containing 10.0 g of trans-(−)-$\Delta^9$-THC) in 65 mL of heptane and crude trans-(+)-$\Delta^9$-THC (24.3 g; containing 10.0 g of trans-(+)-$\Delta^9$-THC), 50% and heptane (315 mL) was admixed with a methanolic caustic solution containing 50% caustic (33 g), water (16.5 mL) and methanol (190 mL) for 20 minutes at 25° C. The resultant purple methanolic caustic (lower) phase was collected, and the organic phase was admixed again with a methanolic caustic solution containing 50% caustic (33 g), water (16.5 mL) and methanol (190 mL) for 20 minutes at 25° C. The resultant methanolic caustic phase was collected, and the combined methanolic caustic phases were treated slowly with a 10% solution of citric acid in water (545 g). The resultant yellow admixture was then extracted with heptane (200 g). The resultant organic phase collected and washed with water (150 mL), dried over $Na_2SO_4$, and filtered. The resultant filtrate was dried by azeotropic distillation and concentrated under reduced pressure. The resultant red oil (41.76 g) was dissolved in heptane (57 g), cooled to 0° C., and seeded with 100 mg of crystalline (±)-$\Delta^9$-THC. The resultant admixture was cooled to −15° C. and stirred at −15° C. for 12 hours. The resultant mixture was suction-filtered, and the solids were washed with cold heptane (3×10 mL). The resultant yellow solids were allowed to dry under suction to provide 12.45 g of crude (±)-$\Delta^9$-THC.

The crude (±)-$\Delta^9$-THC (12.45 g) was dissolved in heptane (25 mL) at 50° C., and the resultant solution was cooled to −10° C. for 2-3 hours. The resultant mixture was suction-filtered and the solids washed 3 times with cold heptane (10, 10, and 20 mL). The solids were then allowed to dry under suction to provide (±)-$\Delta^9$-THC as white crystals. Yield: 8.70 g; 14% yield (based on olivetol); 44% yield based on (−)-$\Delta^9$-THC and (+)-$\Delta^9$-THC. Analysis (HPLC) of the crystalline (±)-$\Delta^9$-THC indicated that it had a purity of 96.45%.

5.21. Example 21

Resolution of trans-(−)-$\Delta^9$-THC and trans-(+)-$\Delta^9$-THC from (+)-$\Delta^9$-THC (±)-$\Delta^9$-THC (2.00 g, 97.7% pure) was eluted by flash chromatography on a Merck column (210×50 mm) using Chiralpak® AD™ 20 μm chiral (Daicel, Tokyo, Japan) as the stationary phase (loading capacity 500 mg per injection, UV at 228 nm) and n-heptane:2-propanol (95:5 (v:v)) as the mobile phase at a flow rate of 200 mL/min at 20° to 25° C. The fractions in which only trans-(−)-$\Delta^9$-THC was observed were combined, and the volatiles removed using a rotary evaporator at 35° to 40° C. to provide trans-(−)-$\Delta^9$-THC (1a). Yield: 0.89 g; 89%. Analysis of the product (HPLC) indicated that it was at least 99.9% pure, i.e., no other cannabinoids were detected.

5.22. Example 22

Resolution of trans-(−)-$\Delta^9$-THC and trans-(+)-$\Delta^9$-THC from (±)-$\Delta^9$-THC Crystalline (±)-$\Delta^9$-THC from Example 15 (3.8 g) was dissolved in 8 ml of heptane:2-propanol (95:5 (v:v)) mixture. The resultant solution was injected into a 2 inch stainless steel "Load and Lock" column (Varian) packed with Chiralpak® AD chiral derivatized silica (Chiral Technologies, Inc. Exton, Pa.). Elution was carried out under isocratic conditions with a solution of heptane:isopropanol (95:5 (v:v)) at a temperature of about 25° C. and at a flow rate of 250 mL of eluent/min. Detection of compounds in the eluent was carried out by UV absorption at 235 nm.

Trans-(+)-$\Delta^9$-THC eluted first, and the combined trans-(+)-$\Delta^9$-THC eluents were concentrated under reduced pressure to provide 1.5 g of trans-(+)-$\Delta^9$-THC (1b) as a reddish-yellow oil.

Trans-(−)-$\Delta^9$-THC eluted after the trans-(+)-$\Delta^9$-THC, and the combined trans-(−)-$\Delta^9$-THC eluents were concentrated under reduced pressure to provide trans-(−)-$\Delta^9$-THC (1a) as a thick viscous reddish-yellow oil. Yield: 1.4 g. Analysis (HPLC) of the trans-(−)-$\Delta^9$-THC product indicated that it had a purity of 99.4%.

5.23. Example 23

Resolution of trans-(−)-$\Delta^9$-THC and trans-(+)-$\Delta^9$-THC from (±)-$\Delta^9$-THC Crystalline (±)-$\Delta^9$-THC from Example 13 (about 2.0 g) was dissolved in a about 26 ml of 95:5 heptane:IPA (v:v)

mixture to provide a 10 wt. % solution. A portion of the 10% solution (about 5 g) was injected into 220×50 mm stainless steel column (Merck) packed with Chiralpak® AD 20 μm chiral derivatized silica (Daicel, Tokyo, Japan). Elution was carried out under isocratic conditions with a solution of heptane:2-propanol (95:5 (v:v)) solvent at about 25° C. and at a flow rate of 200 mL of eluent/min. Detection of products in the eluent was carried out by UV absorption at 228 nm. The elution of the remaining portions of the 10% solution was carried on about 3×5 g samples as described above.

The fractions containing (+)-$\Delta^9$-THC were combined and concentrated under reduced pressure to provide (+)-$\Delta^9$-THC as reddish-yellow oil. Yield: 1.0 g. Analysis (HPLC) of the oil indicated that it had a purity of 97.0%.

The fractions containing trans-(−)-$\Delta^9$-THC were combined and concentrated under reduced pressure to provide trans-(−)-$\Delta^9$-THC (1a) as a thick viscous reddish-yellow oil. Yield: 1.0 g. Analysis (HPLC) of the product indicated that it had a purity of 99.9%.

The product was stored in a freezer and protected from light and oxygen.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited, the entire disclosures of which are incorporated herein by reference.

What is claimed:

1. A trans-(−)-$\Delta^9$-tetrahydrocannabinol composition comprising at least 99.0% by weight of trans-(−)-$\Delta^9$-tetrahydrocannabinol and less than 0.05% of $\Delta^9$-tetrahydrocannabinol acid based on the total amount of cannabinoids.

2. The trans-(−)-$\Delta^9$-tetrahydrocannabinol composition of claim 1, comprising at least 99.5% by weight of trans-(−)-$\Delta^9$-tetrahydrocannabinol based on the total amount of cannabinoids.

3. The trans-(−)-$\Delta^9$-tetrahydrocannabinol composition of claim 1, comprising at least 99.9% by weight of trans-(−)-$\Delta^9$-tetrahydrocannabinol based on the total amount of cannabinoids.

4. The trans-(−)-$\Delta^9$-tetrahydrocannabinol composition of claim 1, wherein the composition comprises up to about 99.95% by weight of trans-(−)-$\Delta^9$-tetrahydrocannabinol based on the total amount of cannabinoids.

5. The trans-(−)-$\Delta^9$-tetrahydrocannabinol composition of claim 1, wherein the composition comprises up to about 99.98% by weight of trans-(−)-$\Delta^9$-tetrahydrocannabinol based on the total amount of cannabinoids.

6. The trans-(−)-$\Delta^9$-tetrahydrocannabinol composition of claim 2, wherein the composition comprises up to about 99.95% by weight of trans-(−)-$\Delta^9$-tetrahydrocannabinol based on the total amount of cannabinoids.

7. The trans-(−)-$\Delta^9$-tetrahydrocannabinol composition of claim 2, wherein the composition comprises up to about 99.98% by weight of trans-(−)-$\Delta^9$-tetrahydrocannabinol based on the total amount of cannabinoids.

8. The trans-(−)-$\Delta^9$-tetrahydrocannabinol composition of claim 3, wherein the composition comprises up to about 99.95% by weight of trans-(−)-$\Delta^9$-tetrahydrocannabinol based on the total amount of cannabinoids.

9. The trans-(−)-$\Delta^9$-tetrahydrocannabinol composition of claim 3, wherein the composition comprises up to about 99.98% by weight of trans-(−)-$\Delta^9$-tetrahydrocannabinol based on the total amount of cannabinoids.

10. The trans-(−)-$\Delta^9$-tetrahydrocannabinol composition of claim 1, wherein the composition comprises less than 0.01% of $\Delta^9$-tetrahydrocannabinol acid based on the total amount of cannabinoids.

11. The trans-(−)-$\Delta^9$-tetrahydrocannabinol composition of claim 2, wherein the composition comprises less than 0.01% of $\Delta^9$-tetrahydrocannabinol acid based on the total amount of cannabinoids.

12. The trans-(−)-$\Delta^9$-tetrahydrocannabinol composition of claim 3, wherein the composition comprises less than 0.01% of $\Delta^9$-tetrahydrocannabinol acid based on the total amount of cannabinoids.

13. The trans-(−)-$\Delta^9$-tetrahydrocannabinol composition of claim 4, wherein the composition comprises less than 0.01% of $\Delta^9$-tetrahydrocannabinol acid based on the total amount of cannabinoids.

14. The trans-(−)-$\Delta^9$-tetrahydrocannabinol composition of claim 5, wherein the composition comprises less than 0.01% of $\Delta^9$-tetrahydrocannabinol acid based on the total amount of cannabinoids.

15. The trans-(−)-$\Delta^9$-tetrahydrocannabinol composition of claim 6, wherein the composition comprises less than 0.01% of $\Delta^9$-tetrahydrocannabinol acid based on the total amount of cannabinoids.

16. The trans-(−)-$\Delta^9$-tetrahydrocannabinol composition of claim 7, wherein the composition comprises less than 0.01% of $\Delta^9$-tetrahydrocannabinol acid based on the total amount of cannabinoids.

17. The trans-(−)-$\Delta^9$-tetrahydrocannabinol composition of claim 8, wherein the composition comprises less than 0.01% of $\Delta^9$-tetrahydrocannabinol acid based on the total amount of cannabinoids.

18. The trans-(−)-$\Delta^9$-tetrahydrocannabinol composition of claim 9, wherein the composition comprises less than 0.01% of $\Delta^9$-tetrahydrocannabinol acid based on the total amount of cannabinoids.

* * * * *